US010921322B2

(12) United States Patent
Castrop

(10) Patent No.: US 10,921,322 B2
(45) Date of Patent: Feb. 16, 2021

(54) METHODS FOR DETECTING A MARKER FOR ACTIVE TUBERCULOSIS

(71) Applicants: KEI INTERNATIONAL LIMITED, Hong Kong (HK); TOMORROWS IP LIMITED, Hong Kong (HK)

(72) Inventor: Johannes Theodorus Castrop, Woudenberg (NL)

(73) Assignees: KEI INTERNATIONAL LIMITED, Hong Kong (HK); TOMORROWS IP LIMITED, Hong Kong (HK)

( * ) Notice: Subject to any disclaimer, the term of this patent is extended or adjusted under 35 U.S.C. 154(b) by 0 days.

(21) Appl. No.: 15/541,683

(22) PCT Filed: Jan. 4, 2016

(86) PCT No.: PCT/NL2016/050002
§ 371 (c)(1),
(2) Date: Jul. 5, 2017

(87) PCT Pub. No.: WO2016/111619
PCT Pub. Date: Jul. 14, 2016

(65) Prior Publication Data
US 2017/0328901 A1 Nov. 16, 2017

(30) Foreign Application Priority Data

Jan. 5, 2015 (NL) .................................... 2014085
Oct. 2, 2015 (NL) .................................... 2015553

(51) Int. Cl.
| | | |
|---|---|---|
| G01N 33/569 | (2006.01) | |
| G01N 33/92 | (2006.01) | |
| G01N 33/50 | (2006.01) | |
| G01N 33/543 | (2006.01) | |
| A61B 5/15 | (2006.01) | |
| A61B 5/157 | (2006.01) | |
| B01L 3/00 | (2006.01) | |
| G01N 33/554 | (2006.01) | |

(52) U.S. Cl.
CPC ....... *G01N 33/56933* (2013.01); *A61B 5/157* (2013.01); *A61B 5/150022* (2013.01); *A61B 5/150251* (2013.01); *A61B 5/150755* (2013.01); *B01L 3/502* (2013.01); *G01N 33/502* (2013.01); *G01N 33/543* (2013.01); *G01N 33/54306* (2013.01); *G01N 33/54386* (2013.01); *G01N 33/569* (2013.01); *G01N 33/92* (2013.01); *B01L 2200/10* (2013.01); *B01L 2300/0636* (2013.01); *B01L 2300/0672* (2013.01); *B01L 2300/0681* (2013.01); *B01L 2300/087* (2013.01); *B01L 2300/0864* (2013.01); *G01N 2333/35* (2013.01); *G01N 2469/20* (2013.01)

(58) Field of Classification Search
None
See application file for complete search history.

(56) References Cited

U.S. PATENT DOCUMENTS

| 7,851,166 B2 | 12/2010 | Verschoor et al. ............. 435/7.2 |
| 2009/0111125 A1* | 4/2009 | Verschoor .......... G01N 33/5695 |
| | | 435/7.21 |

FOREIGN PATENT DOCUMENTS

| RU | 2 470 801 | 6/2011 | ................ B60P 3/00 |
| WO | WO2005116654 | 12/2005 | ........... G01N 33/569 |
| WO | WO 2012/119128 | 3/2012 | ................ B01L 3/00 |
| WO | WO2013186679 | 12/2013 | ........... G01N 33/543 |
| WO | WO2014184768 | 11/2014 | ........... G01N 33/569 |

OTHER PUBLICATIONS

Thanyani et al. Journal of Immunological Methods vol. 332, pp. 61-72 , 2008 (Year: 2008).*
Boulos et al. Journal of Public Health Informatics 5(3) 2014. (Year: 2014).*
Chamanzar et al., "Hybrid photonic surface-plasmon-polariton ring resonators for sensing applications," Applied Physics B, vol. 101, No. 1-2, Oct. 2010, pp. 263-271 (9 pgs).
Hermanson, G., "Bioconjugate Techniques," Academic Press, $3^{rd}$ Edition, Aug. 2013, book description only (3 pgs).
International Preliminary Report on Patentability issued in application No. PCT/NL2016/050002, dated Dec. 19, 2016 (30 pgs).
International Search Report and Written Opinion issued in application No. PCT/NL2016/050002, dated Jun. 30, 2016 (13 pgs).
Law, B., "Immunoassay: a practical guide," Taylor & Francis e-Library, 2005 (15 pgs).
Lemmer et al., "Detection of Antimycolic Acid Antibodies by Liposomal Biosensors," Methods in Enzymology, No. 464, Jan. 2009, pp. 79-104 (26 pgs).
Mathebula et al., "Recognition of anti-mycolic acid antibody at self-assembled mycolic acid antigens on a gold electrode: a potential impedimetric immunosensing platform for active tuberculosis," Chemical Communications, No. 23, May 2009, pp. 3345-3347 (3 pgs).
Thanyani et al., "A novel application of affinity biosensor technology to detect antibodies to mycolic acid in tuberculosis patients," Journal of Immunological Methods, vol. 332, Jan. 2008, pp. 61-72 (12 pgs).
Thanyani, S.T., "An assessment of two evanescent field biosensors in the development of an immunoassay for tuberculosis," partial fulfillment of the requirements for the PhD Degree in Biochemistry in the Faculty of Natural & Agricultural Sciences, University of Pretoria, Jul. 2008 (194 pgs).

(Continued)

*Primary Examiner* — Jana A Hines
*Assistant Examiner* — Khatol S Shahnan Shah
(74) *Attorney, Agent, or Firm* — Hayes Soloway P.C.

(57) ABSTRACT

Provided are methods of detecting a marker for active tuberculosis, and a portable device for carrying out a method of detecting a marker for active tuberculosis. Also provided is a system for carrying out a method of detecting a marker for active tuberculosis, a method for pre-treating a sample stream from a human or animal suspected of having active tuberculosis, a system for pre-treating a sample stream from a human or animal suspected of having active tuberculosis and kits for performing said methods.

25 Claims, 2 Drawing Sheets

(56) References Cited

OTHER PUBLICATIONS

Tiwari et al., "Glycolipids of *Mycobactrium tuberculosis* Strain H37Rv Are Potential Serological Markers for Diagnosis of Active Tuberculosis," Clinical and Diagnostic Laboratory Immunology, vol. 12, No. 3, Mar. 2005, pp. 465-473 (9 pgs).

Hamilton et al., "Naturally occurring carbohydrate antibodies: Interference in solid-phase imunoassays" *Journal of Immunological Methods*, vol. 77, Issue 1, Feb. 28, 1985, pp. 95-108, Abstract only (2 pgs).

\* cited by examiner

METHODS FOR DETECTING A MARKER FOR ACTIVE TUBERCULOSIS

The present invention relates to methods of detecting a marker for active tuberculosis, a portable device for carrying out a method of detecting a marker for active tuberculosis. The present invention further a system for carrying out a method of detecting a marker for active tuberculosis, a method for pre-treating a sample stream from a human or animal suspected of having active tuberculosis, a system for pre-treating a sample stream from a human or animal suspected of having active tuberculosis and kits for use in said methods.

INTRODUCTION

*Mycobacterium tuberculosis* is a pathogenic bacterial species in the family Mycobacteriaceae and the causative agent of most cases of tuberculosis (TB).

Nine million people fell ill with TB in 2013, including 1.5 million cases among people with HIV. In 2013, 1.5 million people died from TB, including 360000 among people who were HIV-positive. TB is one of the top three killers of women worldwide, 510000 women died from TB in 2013. Of the TB deaths among HIV-positive people, 50% were among women. At least 550000 children became ill with TB and an estimated 80 000 children who were HIV-negative died of TB in 2013. Globally in 2013, an estimated 480000 people developed multidrug-resistant TB (MDR-TB) and there were an estimated 210000 deaths from MDR-TB. At least one case of extensively drug-resistant TB (XDR-TB) has been reported by 100 countries by the end of 2013. On average, an estimated 9% of MDR-TB cases have XDR-TB.

A reliable and fast way of diagnosing tuberculosis is therefore of utmost importance.

Several methods of diagnosing tuberculosis have been developed, but all methods have their disadvantages. Diagnosing active tuberculosis based merely on signs and symptoms is difficult, as is diagnosing the disease in those who are immunosuppressed. The TB skin test (also called the Mantoux tuberculin skin test), TB blood tests (also called interferon-gamma release assays or IGRAs), and chest radiography (X-ray), and tests on the presence of acid-fast-bacilli (AFB) on a sputum smear, indicate some of the infected individuals in days. A definitive diagnosis of TB is made by identifying *M. tuberculosis* in a clinical sample (e.g. sputum, pus, or a tissue biopsy). However, the difficult culture process for this slow-growing organism can take two to six weeks for blood or sputum culture.

Humans or animals infected with the *M. tuberculosis* normally produce antibodies directed against the *Mycobacterium*. Presence of these antibodies in a sample taken from infected individuals indicates the infection. WO 2005/116654 describes a method based on this principle and discloses detecting a marker for active tuberculosis. The method of WO 2005/116654 involves obtaining first, second and third samples from a subject suspected of having active tuberculosis, diluting the first sample and exposing part of it to an immobilized mycolic acid antigen in a test vessel and part of it to an immobilized mycolic antigen in a control vessel. The second sample is exposed to mycolic acid antigen-containing liposomes and the third sample is exposed to liposomes not containing mycolic acid antigens. The second sample is added to the test vessel and the third to the control vessel and binding of antibodies to the mycolic acid and antigen in both the test and control vessel is detected. The degree of binding between the test and control vessels is compared and lesser binding in the test vessel is an indicator of the presence of antibodies to the mycolic acid antigen.

A further development was described in WO 2013/186679, which discloses a method of detecting antigen specific biomarker antibodies for the diagnosis of active tuberculosis, the method including the steps of: providing a lipid antigen-presenting liposomal composition comprising liposomes comprising a sterol-modified lipid and a purified mycobacterial lipid cell wall component or analogue or derivative thereof; immobilizing the liposomes to produce immobilized mycolic acid antigens comprising the purified mycobacterial lipid cell wall component or analogue or derivative thereof; obtaining a first, a second and a third sample from a human or animal suspected of having active tuberculosis, wherein each sample may contain antibodies to the antigen, the first sample having a lower concentration by dilution than the second and third samples; exposing part of the first sample to the immobilized mycolic acid antigens in a test vessel; exposing part of the first sample to the immobilized mycolic acid antigens in a control vessel; exposing the second sample to the lipid antigen-presenting liposomal composition provided in the first step; exposing the third sample to liposomes not containing mycolic acid antigen; adding the second sample, after exposure to the mycolic acid antigen-containing liposomal composition provided in the first step, to the test vessel; adding the third sample, after exposure to the liposomes not containing mycolic acid, to the control vessel; detecting binding of antibodies to the mycolic acid antigen in both the test and control vessels in real time; and comparing the degree or extent of binding between the test and the control vessels, the weaker binding in the test vessel being an indicator of the presence of antibodies to the mycolic acid antigen in the sample that indicates active tuberculosis in the human or animal from which the sample originated.

The methods described in WO 2005/116654 and WO 2013/186679 provide reliable methods for diagnosis of tuberculosis, but have several disadvantages. First, the methods described in WO 2005/116654 and WO 2013/186679 require provision of several samples from the same subject. Second, these methods require several dilution steps and several transfer steps of samples to different unconnected compartments, requiring a complicated and large set of instrumental parts. Third, these methods involve separate incubation steps of the sample and dilutions thereof and consequently several separate measurements. For these reasons the methods of WO 2005/116654 and WO 2013/186679 are complicated and time consuming. In fact, the total time from obtaining a sample from a subject suspected of having active tuberculosis to determining whether or not an individual is infected with active tuberculosis using the methods disclosed in WO 2005/116654 and WO 2013/186679 takes an estimated time of at least 2 hours per sample. Furthermore, because the above methods require a complicated and large set of instrumental parts, said methods may be useful in a hospital environment, but not in areas which are deprived from hospitals and well developed healthcare, for instance in developing countries. It is in particular in these countries where tuberculosis is most prevalent and where reliable and fast diagnosis is most desired.

Therefore the invention aims to provide a way to determine whether or not an individual is infected with active tuberculosis (e.g. pulmonary or extra-pulmonary tuberculosis) which is fast and reliable, and which can be carried out outside of a professional medical environment, i.e. outside of a hospital, for instance on the streets.

SUMMARY OF THE INVENTION

In a first aspect the invention relates to a method of detecting a marker for active tuberculosis in an end-point assay as defined in claim 1.

In a second aspect the invention relates to a method for pre-treating a sample from a human or animal suspected of having active tuberculosis as defined in claim 4.

In a third aspect the invention relates to a system for carrying out a method of detecting a marker for active tuberculosis as defined in claim 5.

In a fourth aspect the invention relates to a system for pre-treating a sample from a human or animal suspected of having active tuberculosis as defined in claims 10, 11 and 12.

In a fifth aspect the invention relates to kits as defined in claims 24 and 25.

DESCRIPTION OF THE INVENTION

Figure 1:
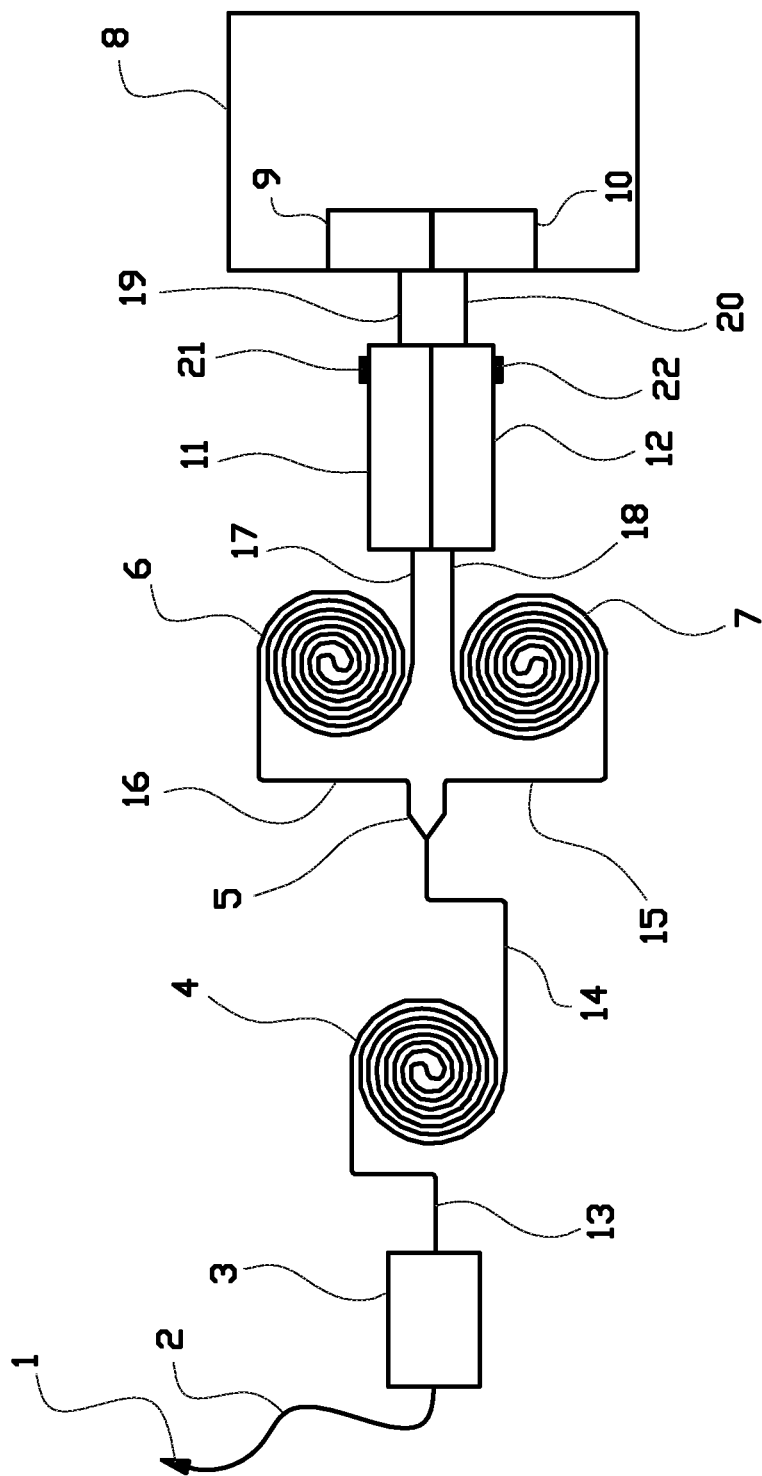
FIG. 1 describes an exemplary embodiment of the device of the invention.
Figure 2:
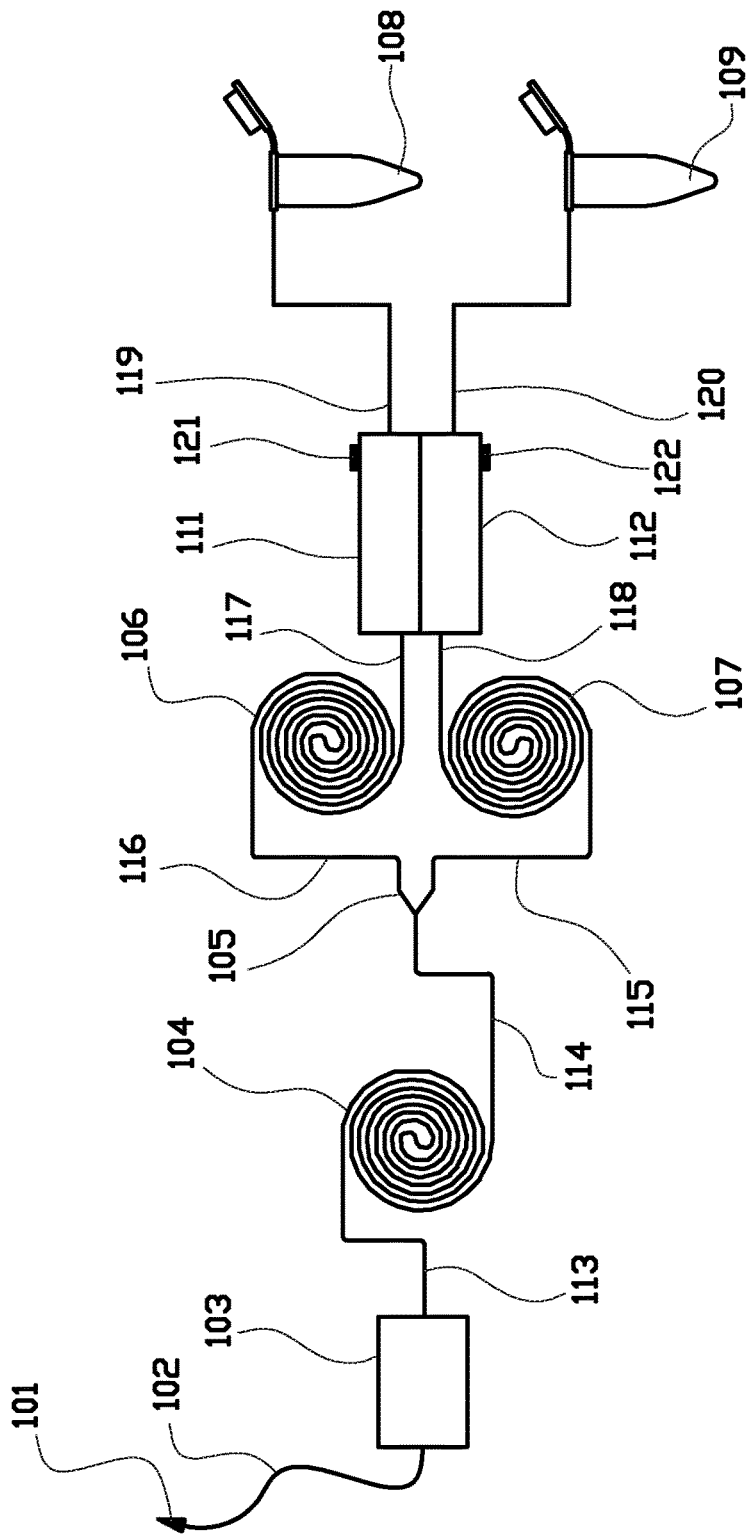
FIG. 2 describes an exemplary embodiment of the system according to claim 17.

The principle of the invention is based on the observation of the inventor that antibodies against mycolic acid derivatives in a sample can be detected fast and reliably if the sample is pretreated in accordance with steps i)-v) of the methods described below.

Real Time Detection Method

The present invention relates in one aspect to a method for detecting antibodies against mycolic acid derivatives, such as cord factors antibodies or mycolic acid (MA) antibodies in a sample, wherein detection takes place in real time.

This method comprises the steps of:

i) providing a sample from a human or animal suspected of having active tuberculosis;

ii) contacting said sample to a sterol lipid;

iii) obtaining at least two fractions of said sample either before or after exposing it to said sterol lipid;

iv) exposing the first of said fractions to a substrate carrying an immobilised mycolic acid derived antigen;

v) exposing the second of said fractions to a substrate not carrying an immobilised mycolic acid derived antigen;

vi) exposing the sample fraction exposed in step iv) to a test substrate carrying an immobilised mycolic acid derived antigen and exposing the sample fraction exposed in step v) to a control substrate carrying an immobilised mycolic acid derived antigen;

vii) detecting binding of antibodies to the antigen of step vi) in real time; and viii) comparing the degree or extent of antibody binding between the test and control substrates, any observed lesser binding to the test substrate being an indicator of the presence of antibodies to the antigen in the sample that indicates active tuberculosis in the human or animal from which the sample originated. This method will be referred to throughout the application as the "real time method"

The real time method enables samples, preferably blood samples to be analyzed in a reliable and fast way without the need to transfer samples from and into several vessels. The subsequent pre-incubation steps of the sample with a sterol lipid, followed by subjecting a fraction of the sample to a pre-incubation step with a mycolic acid derived antigen to obtain a test sample and another fraction of the sample to a pre-incubation without a mycolic acid derived antigen to obtain a control sample render the sample suitable for direct application in the eventual detection step which entails binding of mycolic acid antigens in the pretreated sample to a biosensor substrate carrying a mycolic acid. The biosensor substrate therefore does not require pre-incubation or pre-treatment of the sensor with a dilution of the sample. Accordingly, the method of the invention does not require the several dilution and transfer steps required in methods of the prior art.

Furthermore the real time method of the invention is advantageously suitable for carrying out by means of a portable device, in particular by means of the device defined below. This makes it possible to determine whether or not an individual is infected with active tuberculosis (e.g. pulmonary or extra-pulmonary tuberculosis) in fast and reliable way, allowing detection of tuberculosis in less than 15 to 25 minutes. Furthermore the method can be carried out outside of a professional medical environment.

In particular the real time method provides a quick method for determining whether or not an individual is infected with active tuberculosis as a point of care test i.e. as a test at or near the site of patient care. The test of the present invention provides simple medical tests which can be performed at the bedside.

Furthermore, the real time method only requires taking one sample from a subject, which sample can be used directly in the method of the invention.

The real time method of the invention will now be explained in more detail with reference to the steps of the real time method.

Step i (Real Time Method)

The real time method of the invention is based on diagnostic testing of samples, in particular blood samples of a human or animal suspected of having active tuberculosis. For this purpose in step i) of the real time method of the invention a sample from a human or animal suspected of having active tuberculosis is provided. The sample is preferably a whole blood sample. The sample may be obtained by any regular means of obtaining blood from a subject. In order to be used in the method of the invention samples may be used that have been collected at an earlier stage, stored until use under suitable conditions and provided at a suitable moment. Alternatively, a sample may be used in the method of the invention on the spot, i.e. as a point of care test. In the latter situation the portable device of the invention will be particularly suitable to use In case the sample is a whole blood sample, the sample may depending on the way of detection of binding of antibodies to the antigen be filtered or separated to plasma or serum before step ii). In case the detection is carried out by means detecting mass differences, a filtering step may be preferred to filter out high mass components such as blood cells. In case binding is detected by fluorescence, one may choose not to filter the sample. This would even shorten the time required for diagnosis.

The sample is preferably a blood derived sample. The sample may be a whole blood sample, a plasma sample or a serum sample. Blood serum is blood plasma without clotting factors and is preferred as plasma. The word plasma in this application may therefore as well refer to (blood) serum. The choice of blood plasma or blood serum depends on whether the device of the invention is designed to separate the whole blood into plasma or serum. Serum is preferred because it contains less different materials than blood plasma which may lead to a specific interactions or unwanted biological activity. In addition serum may have a lower viscosity than blood plasma. Using serum therefore may circumvent the need for diluting a sample, which saves time and materials.

About 55% of whole blood consists of plasma/serum. If a whole blood sample is not filtered perfectly or if the patient's physical situation necessitates it, it may be desired to dilute the whole blood sample or plasma or serum. The words plasma or serum in this application may therefore also refer to diluted plasma or serum.

A dilution of the blood or plasma may therefore be implemented in the real time method of the invention, such as a 250 to 5000× dilution, a 750 to 1250× dilution, such as for instance a 4000, 2000 or 1000× dilution. Depending on the viscosity of the sample, such dilution may take place before the separating the plasma from the blood step or after the separating step or alternative to the separating step. For instance the dilution step may take place after the separating step but before step iv) or v) or after step v)/vi) and before step vii). It is preferred to dilute the sample after step v)/vi) and before step vii) i.e. just before the samples enters the biosensor. This way the volume of the sample is kept as low as possible during most of the steps of the method, which is beneficial to the speed of the process and the compactness of the device used therein.

Dilution may be performed with any suitable diluent, for example a PBS based buffer. Such buffer may for example be a PBS/AE buffer comprising NaCl, KCl, $KH_2PO_4$, $Na_2HPO_4$ and EDTA in water at physiological pH. Such buffer may be a PBS based buffer consisting of 8.0 g NaCl, 0.2 g KCl, 0.2 g $KH_2PO_4$, and 1.05 g $Na_2HPO_4$ per liter of double distilled, deionized water containing 1 mM EDTA and 0.025% (m/v) sodium azide which is adjusted to pH 7.4.

The whole blood sample or plasma or serum may be further diluted with agents that prevent blood clotting, such as EDTA, heparine or citrate.

Optionally a detergent may be added in low concentration to the blood/plasma/serum to avoid sticking of components to walls of tubings, vessels or containers.

Step ii (Real Time Method)

In step ii, the sample is exposed to, i.e. contacted with a sterol lipid.

Although the inventors do not wish to be bound by any theory, it is assumed that the sterol lipid scavenges away the anti-cholesterol antibodies from the sample that would otherwise cross react with the mycolic acid antigens on the sensor substrate and lead to false positive diagnosis of tuberculosis.

The exposure time of the sample to the sterol lipid is preferably less than 10 minutes, such as 2 to 8, 3 to 7, 4 to 6 or about 5 minutes. The exposure time depends on the way the sample is brought into contact with the sterol lipid.

One exemplary way of exposing the sample to the sterol lipid is to lead the sample into a long spiral channel and pass it along the length of the channel, which is pre-coated with a sterol lipid, which is preferably cholesterol. At the end of the channel the lipid sterol exposed sample may pass a means for dividing the sample stream such as a passive valved branch point that leads the divided sample streams to the next substrate carrying an immobilised mycolic acid derived antigen of step v) and the substrate not carrying an immobilised mycolic acid derived antigen of step vi), i.e. a container comprising a substrate carrying an immobilised mycolic acid derived antigen, and a container comprising a substrate not carrying an immobilised mycolic, acid derived antigen respectively.

An alternative exemplary way of exposing the sample to the sterol lipid is to inject it into a container coated with cholesterol, followed by incubation therein for less than 10 minutes.

Whole blood/plasma/serum is rich in hundreds different kind of molecules with hydrophilic to hydrophobic properties. Therefore substrate material will be used that is inert for non-specific binding of molecules of this sample. In this context the substrate should be understood to be a support material.

Steps iv and v (Real-Time Method)

In the next step a fraction of the sterol lipid exposed sample is exposed to a substrate carrying an immobilised mycolic acid derived antigen (step iv)) and another fraction of the sterol lipid exposed sample to a substrate not carrying an immobilised mycolic acid derived antigen (step v)).

To obtain at least two fractions, at a certain moment in the process the blood/plasma stream has to be divided (step iii of the real time method). For sake of convenience and to optimize reliability of the method, it is preferred that the stream is divided after exposure to the sterol lipid, i.e. that the sterol lipid exposed sample is divided into at least two fractions to provide a test stream and a control stream. It is preferred that the sample is divided in two equal or substantially equal fractions, because this enables a simple comparison of both fractions without the need for correction calculations. Dividing the sample stream may be carried out by any means for dividing the sample stream such as a passive valved branch point.

Alternatively the sample stream (which is filtered to plasma or serum) is divided into at least two fractions after the filtering step, but before exposure to the sterol lipid. Alternatively the blood stream is divided before filtering. This is less preferred because in this case two filters would be required.

The substrate carrying an immobilised mycolic acid derived antigen and the substrate not carrying an immobilised mycolic acid derived antigen of steps iv) and v) are preferably of the same material.

In addition, since sterol lipids, (e.g. cholesterol) and mycolic acid derivatives are both hydrophobic, the substrates for exposure in steps iv) and v) will be of the same material as the substrate that may be used to in step ii). It will be understood that suitable substrate material is inert for non-specific binding of molecules of this sample.

The exposure time of the sample to the sterol lipid is preferably less than 10 minutes, such as 2 to 8, 3 to 7, 4 to 6 or about 5 minutes.

One exemplary way of exposing the sample to the substrates of step iv) and v) is to lead the divided sample streams into long spiral channels, preferably implemented in microchips, pre-coated either with a mycolic acid derivative (step iv) or without a mycolic acid derivative (step v) and pass it along the length of these channels. The distance of both channels to the biosensor will need to be of the same length. It is important that there is as less as possible non-specific binding the substrate material.

An alternative exemplary way of exposing the divided lipid sterol exposed samples to a substrate coated either with a mycolic acid derivative or without a mycolic acid derivative is to inject the a first stream into a container comprising a substrate carrying an immobilised mycolic acid derived antigen (step iv), and a second sample stream into a container comprising a second substrate not carrying an immobilised mycolic acid derived antigen (step v) and incubate the samples for less than 10 minutes, such as 2 to 8, 3 to 7, 4 to 6 or about 5 minutes.

Step vi (Real Time Method)

In this step the divided sterol lipid exposed sample streams, either exposed to mycolic acid derivatives in step iv(test stream) or not in step v (control stream) are passed to further substrates, test and control substrates respectively, carrying mycolic acid derivatives, preferably the same derivatives as in step iv.

These test and control substrates are contained in a biosensor comprising a first chamber (test chamber) with a test substrate for receiving the test stream exposed to mycolic acid derivatives in step iv), and in a second chamber (control chamber) with a control substrate for receiving the control stream not exposed to mycolic acid derivatives in step v). The substrates in both chambers are preferably of the same material and carry the same mycolic acid derivative. A biosensor is in this context can be any means capable to generate a measurable signal when antibodies contact the mycolic acid derivatives on the test and control substrates.

Preferably the test and control substrates of step vi) are silica based, such as substrates based on silicium dioxide. Silica based substrates are particularly useful when ring resonance technology is used to detect binding of antibodies to the immobilised mycolic acid antigens. Preferably the detection is carried out using a biosensor chip using Si-based ring resonator. This enables the method of the invention to be carried out with a very compact device.

It is also well possible that the substrates of step vi) are gold based. Gold based substrates are particularly useful when surface plasmon resonance or electrochemical impedance spectroscopy are used to detect binding of antibodies to the immobilised mycolic acid antigens.

Steps vii and viii (Real Time Method)

In step vii the binding of antibodies to the immobilised mycolic acid antigens is detected. Because detection takes place in real time, binding of antibodies on the substrates of step vi is directly detected during the binding process. It is therefore to be understood that steps vi and vii are not steps that need to take place at separate times. This also applies for step viii, i.e. comparison of binding to test and control substrates and detection may take place while the binding process of step vii is still going on. For detection in principle all real-time, label free analysis techniques may be used, such as surface plasmon resonance or electrochemical impedance spectroscopy isothermal titration calorimetry, bio-layer interferometry, optical, gratings, photonic crystal, acoustic resonant profiling, quartz crystal microbalances.

The detection of binding of antibodies and/or other material to the mycolic acid antigen may be carried out in an automated device. Various automated devices will be known to the person skilled in the art and the skilled person will be able to select suitable software means to make the comparison of step viii) of the degree or extent of binding between the test and control substrates, wherein any observed lesser binding to the test substrate is an indicator of the presence of antibodies to the antigen in the samples that relates to active tuberculosis in the human or animal from which the samples originated. In this context it should be understood that lesser can be interpreted qualitatively and quantitatively, i.e. lesser binding may be interpreted as having less binding events as well as having weaker bindings.

Device for Carrying Out Real Time Method

In another aspect the invention relates a portable device for carrying out a real time method of detecting a marker for active tuberculosis, comprising at least one container comprising a sterol lipid arranged and configured to receive a sample stream from a human or animal suspected of having active tuberculosis; means for dividing said sample stream into at least a first and a second sample stream; said means either connected upstream or downstream of said at least one container comprising a sterol lipid; a further container for receiving said first sample stream in downstream connection with a said container comprising a sterol lipid, and comprising a first substrate carrying an immobilised mycolic acid derived antigen; a still further container for receiving the second sample stream in parallel arrangement to said further container and in downstream connection with a said container comprising a sterol lipid; and comprising a second substrate not carrying an immobilised mycolic acid derived antigen, and a biosensor comprising a first chamber for receiving the first sample stream in connection with said further container, comprising a substrate carrying an immobilised mycolic acid derived antigen and a second chamber for receiving the second sample stream in connection with said still further container comprising the same substrate carrying an immobilised mycolic acid derived antigen as the first chamber.

Preferably the device of the invention comprises a skin penetrating end connected to a first tubing, which is arranged and configured receive a blood sample from the skin penetrating end and to carry said blood sample away from the skin site to said container comprising a sterol lipid.

In another preferred embodiment the device comprises a filter unit in connection with said first tubing for receiving said blood sample and configured to separate plasma from said whole blood sample.

In a further preferred embodiment the portable device comprises a skin penetrating end connected to a first tubing, which is arranged and configured receive a blood sample from the skin penetrating end and to carry said blood sample away from the skin site; a filter unit in connection with said first tubing for receiving said blood sample and configured to separate plasma from said whole blood sample; a first container for receiving said sample, said first container comprising a sterol lipid; means for dividing said sample into at least a first and a second sample stream; a second container for receiving said first sample stream, said second container comprising a first substrate carrying an immobilised mycolic acid derived antigen; a third container for receiving the second sample stream, said third container comprising a second substrate not carrying an immobilised mycolic acid derived antigen; and a biosensor comprising a first chamber for receiving the first sample stream in connection with the second container, comprising a substrate carrying an immobilised mycolic acid derived antigen and a second chamber for receiving the second sample stream in connection with the third container comprising the same substrate carrying an immobilised mycolic acid derived antigen as the first chamber.

The stream through the apparatus is preferably driven by a pump, preferably a continuous flow pump, for example a peristaltic pump or a diaphragm pump. The pump is preferably located downstream of the biosensor, in order to be able to suck the sample through the apparatus and to prevent contamination of the sample before analysis.

The skin penetrating means may be any suitable means to obtain a blood sample from a human or animal, such as a needle syringe or the like.

The first tubing has dimensions that are suitable for purpose of the device, i.e. it needs to be well adaptable to the skin penetrating means and the first container.

The components of the device, i.e. the containers, means for diluting, filter unit and biosensor may be interconnected by suitable interlinking tubings. Alternatively the components of the device may be designed such that they can be connected directly to each other. The material of the tubings used in the invention can be any suitable material which is known to the person skilled in the field of testing blood samples. Suitable materials are inert to blood/plasma/serum components and include polytetrafluorethylene (e.g. Teflon®), polypropylene, polyetherketone (PEEK) and polyethylene.

Further components may be connected between the components of the device. Such further components may be connected in tubings interlinking the components are directly attached to the components.

The device of the invention may also comprise a means for dilution of the blood or plasma. Such means may be implemented before the sterol lipid containing container, before the filter unit, between the filter unit and the sterol lipid containing container, between the sterol containing container and the other (further and still further or (second and third) containers or between the further/still further or second/third containers and the respective chambers of the biosensor. Preferably the means for diluting the sample are connected between the further or second container and the biosensor and between the still further or, third container and the biosensor. For instance a 10 ml container may be implemented at the outlet of the further or second and still further or third containers. A suitable buffer may already be present in the container or be added into this container to provide the desired dilution. This way the volume of the sample is kept as low as possible during most of the steps of the method of the invention, which is beneficial to the speed of the process and the compactness of the device of the invention.

The containers may be vessels or a channel or tubing, such as a spiral channel or spiral tube. A spiral channel or tube is preferred because such structure takes little space whilst maintaining a long flow path. A spiral channel or tube may be advantageously implemented on a micro-chip. This contributes to the compactness of the device of the invention.

The filter unit may comprise a filter matrix. Preferably the filter is implemented on a filter microchip for the sake of compactness.

The material of the containers is preferably the same and suitable materials may be bk-7 glass, polytetrafluor-ethyleen, polypropylene, polyether ketone or polyethylene.

The substrates of the containers have to be material that is inert for non-specific binding of molecules of the sample, for instance bk-7 glass, polytetrafluor-ethyleen, polypropylene, polyether ketone or polyethylene.

The device comprises a container comprising a substrate carrying an immobilised mycolic acid derived antigen (second container) and a container comprising a substrate not carrying an immobilised mycolic acid derived antigen. Instead of an immobilised mycolic acid derived antigen, the latter container may an inert coating or no coating, as long as no a specific binding takes place.

Preferably the test and control substrates of the chambers of the biosensor are silica based, such as substrates based on silicium dioxide. Silica based substrates are particularly useful when ring resonance technology is used to detect binding of antibodies to the immobilised mycolic acid antigens.

The biosensor comprises a first and a second chamber. It is to be understood that the two chambers do not need to be in one compartment or housing. For instance the biosensor can comprise two separate sensor units each comprising a chamber with a substrate carrying mycolic acid derivative antigens, one sensor unit being in connection via a tubing with a container comprising a substrate carrying an immobilised mycolic acid derived antigen, the other sensor unit being in connection via a tubing with a container comprising a substrate not carrying an immobilised mycolic acid derived antigen.

Preferably, the biosensor comprises a Si-based ring resonator. This enables the device of the invention to be very compact.

In this respect the invention also relates to a biosensor, comprising at least two chambers comprising a silica based of substrate with an immobilised mycolic acid derived antigen and a Si ring resonator.

It is also well possible that the substrates of the chambers of the biosensor are gold based. Gold based substrates are particularly useful when surface plasmon resonance or electrochemical impedance spectroscopy are used to detect binding of antibodies to the immobilised mycolic acid antigens.

The device of the invention may be connected to any suitable automated analysis means, such as a computer with suitable software programs to carry out the comparison of binding of mycolic acid antibodies to the immobilised antigens in the chambers of the biosensor.

An exemplary embodiment of the device of the invention is shown in FIG. 1.

FIG. 1 shows a skin penetrating needle 1 connected to a first tubing 2, which is arranged and configured receive blood from the needle 1 and to carry the amount of blood away from the skin site. Tubing 1 is connected to a filter unit 3. This filter unit serves to separating plasma from said whole blood sample. Filter unit 3 is connected via tubing 13 to a first container 4, which is in the form of a spiral channel of which the inner wall is coated with a sterol lipid. The spiral channel is connected via tubing 14 with a means for dividing plasma 5 in the form of a passive valved branch point. One branch of the branch point is connected via tubing 16 with a second container 6 for receiving a first plasma stream, which comprises a first substrate carrying an immobilised mycolic acid derived antigen. The other branch of the branch point is connected via tubing 15 with a third container 7 for receiving a second plasma stream, which comprises a second substrate not carrying an immobilised mycolic acid derived antigen. Containers 6 and 7 in this embodiment are in the of a spiral channel of which the inner wall is either coated with a mycolic acid derived antigen (container 6) or not coated with a mycolic acid derived antigen (container 7). Containers 6 and 7 are connecter via respectively tubings 17 and 18 with dilution containers 11 and 12 respectively. These containers may be prefilled with a suitable dilution buffer of comprise inlets 21, 22 for introducing a dilution buffer. The dilution containers 21 and 22 are connected via respective tubings 19 and 20 to a test chamber 9 of a biosensor 8 and to a control chamber 10 of biosensor 8 respectively. The test and control chambers 9 and 10 both comprise the same substrate carrying an immobilised mycolic acid derived antigen.

Kit

In another aspect the invention relates to a kit for use in diagnosing tuberculosis using a real time detection method, comprising one or more skin penetrating means; one or more tubings; one or more containers coated with a sterol lipid and optionally phosphatidyl choline, pectin, amphothericin B or β-cyclodextrin; one or more containers comprising a substrate with an immobilised mycolic acid derived antigen; one or more containers comprising a substrate without an immobilised mycolic acid derived antigen; and one or more biosensors comprising at least two chambers comprising a substrate with an immobilised mycolic acid derived antigen; and optionally means for diluting blood or plasma and/or a filter unit.

The kit may also comprise tools to assemble the components, such as screws, clamps, glue, tape, screwdrivers etc.

The kit may also comprise means to dilute the blood or plasma during blood analysis. Such as container (for instance of 10 ml) to be implemented at the outlet of the second and third containers. A suitable buffer may already be present in the container or be added into this container to provide the desired dilution.

The components of the kit enable the person that is to perform a tuberculosis diagnosis test to assemble the device of the invention on the spot, i.e. at the point of care. It is therefore to be understood that the components of the kit have the same characteristics and preferred properties as explained above for the device of the invention. The device of the invention is easy to be assembled by means of the components of the kit of the invention, i.e. no specialist technical background is required. The kit may be provided conveniently with instructions for assembly and use.

End-Point Method

The present invention relates in a further aspect to a detection method for detecting antibodies against mycolic acid derivatives, such as cord factors antibodies or mycolic acid (MA) antibodies in a sample, wherein detection takes place by means of an end-point assay.

This method comprises the steps of:
i) providing a sample from a human or animal suspected of having active tuberculosis;
ii) contacting said sample to a sterol lipid;
iii) obtaining at least two fractions of said sample either before or after exposing it to said sterol lipid;
iv) exposing the first of said fractions to a substrate carrying an immobilised mycolic acid derived antigen;
v) exposing the second of said fractions to a substrate not carrying an immobilised mycolic acid derived antigen;
vi) exposing at least part of the sample fraction exposed in step iv) to a test substrate carrying an immobilised mycolic acid derived antigen and exposing at least part of the sample fraction exposed in step v) to a control substrate carrying an immobilised mycolic acid derived antigen;
vii) detecting binding of antibodies to the antigen of step vi) in an end-point assay; and
viii) comparing the degree or extent of antibody binding between the test and control substrates, any observed lesser binding to the test substrate being an indicator of the presence of antibodies to the antigen in the sample that indicates active tuberculosis in the human or animal from which the sample originated. This method will be referred to throughout the application as the "end-point method".

The pre-treatment steps i)-v) do not necessarily have to be followed directly by the detection steps vi-viii). For instance the samples fractions obtained after step v) can be stored until further use or for transport to the detection substrate. This way the practiser has great flexibility in planning his test. For instance, the fact that steps i)-iv) do not necessarily have to be followed by steps vi)-viii) allows pre-treated samples to be collected, so that they can be tested all at once on one substrate material, which improves reliability and reproducibility. This also makes it easier to test samples from multiple patients under the same conditions.

Therefore, in another aspect the invention also relates to a method for pre-treating a sample from a human or animal suspected of having active tuberculosis for detection:
i) providing a sample from a human or animal suspected of having active tuberculosis;
ii) exposing said sample to a sterol lipid;
iii) obtaining at least two fractions of said sample either before Or after exposing it to said sterol lipid;
iv) exposing the first of said fractions to a substrate carrying an immobilised mycolic acid derived antigen;
v) exposing the second of said fractions to a substrate not carrying an immobilised mycolic acid derived antigen;
wherein after exposure in steps iv) and v) at least part of the sample fractions are stored for further use. This method will be referred to throughout the application as the "pre-treatment method".

Also the end-point method of the invention enables samples, preferably blood samples to be analyzed in a reliable and fast way. The subsequent pre-incubation steps i)-v) of the sample with a sterol lipid, followed by subjecting a fraction of the sample to a pre-incubation step with a mycolic acid derived antigen to obtain a test sample and another fraction of the sample to a pre-incubation without a mycolic acid derived antigen to obtain a control sample render the sample suitable for direct application in the eventual end-point detection step which entails binding of mycolic acid antigens in the pretreated sample to a substrate carrying a mycolic acid. The substrate therefore does not require pre-incubation or pretreatment with a dilution of the sample. Accordingly, the several dilution and transfer steps required in methods of the prior art are not required.

Furthermore the end-point method makes it possible to determine whether or not an individual is infected with active tuberculosis (e.g. pulmonary or extra-pulmonary tuberculosis) in fast and reliable way, allowing detection of tuberculosis in less than 15 to 25 minutes. This is in particular due to the pretreatment steps i)-v) of the end point method and pre-treatment method. Furthermore the end-point method can be carried out outside of a professional medical environment. In particular herewith a quick method is provided for determining whether or not an individual is infected with active tuberculosis as a point of care test i.e. as a test at or near the site of patient care. The test of the present invention provides simple medical tests which can be performed at the bedside.

Furthermore, because of the pre-treatment steps i)-v) taking one sample from a subject is sufficient, which sample can be used directly for detection without further treatment.

The principle of this aspect of the invention will now be explained in more detail with reference to the steps of the end point method and pre-treatment method.

Step i (End-Point Method/Pre-Treatment Method)

The end-point detection method of the invention is based on diagnostic testing of samples, in particular blood samples of a human or animal suspected of having active tuberculosis. For this purpose in step i) of a sample from a human or animal suspected of having active tuberculosis is provided. The sample is preferably a whole blood sample. The sample may be obtained by any regular means of obtaining blood from a subject. In order to be used in the methods of the invention samples may be used that have been collected at an earlier stage, stored until use under suitable conditions and provided at a suitable moment. Alternatively, a sample may be used in the detection method of the invention on the spot, i.e. as a point of care test. Another alternative is that the sample is pretreated on the spot in accordance with abovementioned steps i)-v), and that the resulting pre-treated samples are stored until further use and/or transferred to another location where detection takes place.

In case the sample is a whole blood sample, the sample may, depending on the way of detection of binding of antibodies to the antigen, be filtered or separated to plasma or serum before step ii). In case the detection is carried out by means detecting mass differences, a filtering step may be preferred to filter out high mass components such as blood cells. In case binding is detected by fluorescence, one may choose not to filter the sample. This would even shorten the time required for pre-treatment and diagnosis.

The sample is preferably a blood derived sample. The sample may be a whole blood sample, a plasma sample or a serum sample. Blood serum is blood plasma without clotting factors and is preferred as plasma. The word "plasma" in this application may therefore as well refer to (blood) serum. The choice of blood plasma or blood serum depends on whether the device of the invention is designed to separate the whole blood into plasma or serum. Serum is preferred because it contains less different materials than blood plasma which may lead to a specific interactions or unwanted biological activity. In addition, serum may have a lower viscosity than blood plasma. Using serum therefore may circumvent the need for diluting a sample, which saves time and materials.

About 55% of whole blood consists of plasma/serum. If a whole blood sample is not filtered perfectly or if the patient's physical situation necessitates it, it may be desired to dilute the whole blood sample or plasma or serum. The words plasma or serum in this application may therefore also refer to diluted plasma or serum.

A dilution of the blood or plasma may be implemented in the methods of the invention. A dilution of 10× to 250× is preferred, in particular when the end-point assay applied is an immunogold filtration assay, such as a dot immunogold filtration assay. Depending on the viscosity of the sample, such dilution may take place before the separating the plasma from the blood step or after the separating step or alternative to the separating step. For instance the dilution step may take place after the separating step but before step iv) or v) or after step v)/vi) and before step vii).

Dilution may be performed with any suitable diluent, for example a PBS based buffer. Such buffer may for example be a PBS/AE buffer comprising NaCl, KCl, $KH_2PO_4$, $Na_2HPO_4$ and EDTA in water at physiological pH. Such buffer may be a PBS based buffer consisting of 8.0 g NaCl, 0.2 g KCl, 0.2 g $KH_2PO_4$, and 1.05 g $Na_2HPO_4$ per liter of double distilled, deionized water containing 1 mM EDTA and 0.025% (m/v) sodium azide which is adjusted to pH 7.4.

The whole blood sample or plasma or serum may be further diluted with agents that prevent blood clotting, such as EDTA, heparine or citrate.

Optionally a detergent may be added in low concentration to the blood/plasma/serum to avoid sticking of components to walls of tubings, vessels or containers.

Step ii (End-Point Method/Pre-Treatment Method)

In step ii, the sample is exposed to, i.e. contacted with a sterol lipid.

Although the inventor does not wish to be bound by any theory, it is assumed that the sterol lipid scavenges away the anti-cholesterol antibodies from the sample that would otherwise cross react with the mycolic acid antigens on the substrate and lead to false positive diagnosis of tuberculosis.

The exposure time of the sample to the sterol lipid is preferably less than 10 minutes, such as 2 to 8, 3 to 7, 4 to 6 or about 5 minutes. The exposure time depends on the way the sample is brought into contact with the sterol lipid.

One exemplary way of exposing the sample to the sterol lipid is to lead the sample into a long spiral channel and pass it along the length of the channel, which is pre-coated with a sterol lipid, which is preferably cholesterol. At the end of the channel the lipid sterol exposed sample may pass a means for dividing the sample stream such as a passive valved branch point that leads the divided sample streams to the next substrate carrying an immobilised mycolic acid derived antigen of step v) and the substrate not carrying an immobilised mycolic acid derived antigen of step vi), i.e. a container comprising a substrate carrying an immobilised mycolic acid derived antigen, and a container comprising a substrate not carrying an immobilised mycolic acid derived antigen respectively.

An alternative exemplary way of exposing the sample to the sterol lipid is to inject it into a container coated with cholesterol, followed by incubation therein for less than 10 minutes.

Another alternative exemplary way is to expose the sample to the sterol lipid, wherein the sterol lipid is contained in a compartment of a column. In such a compartment the sterol lipid is preferably coated on beads.

Whole blood/plasma/serum is rich in hundreds different kind of molecules with hydrophilic to hydrophobic properties. Therefore substrate material will be used that is inert for non-specific binding of molecules of this sample. In this context the substrate should be understood to be a support material.

Steps iv and v (End-Point Method/Pre-Treatment Method)

In the next step a fraction of the sterol lipid exposed sample is exposed to a substrate carrying an immobilised mycolic acid derived antigen (step iv)) and another fraction of the sterol lipid exposed sample to a substrate not carrying an immobilised mycolic acid derived antigen (step v)).

To obtain at least two fractions, at a certain moment in the process the blood/plasma stream has to be divided (step iii). For sake of convenience and to optimize reliability of the method, the stream may be divided after exposure to the sterol lipid, i.e. that the sterol lipid exposed sample is divided into at least two fractions to provide a test stream and a control stream. It is preferred that the sample is divided in two equal or substantially equal fractions, because this enables a simple comparison of both fractions without the need for correction calculations. Dividing the sample stream may be carried out by any means for dividing the sample stream such as a passive valved branch point.

Alternatively the sample stream (which is filtered to plasma or serum) is divided into at least two fractions after the filtering step, but before exposure to the sterol lipid. Alternatively the blood stream is divided before filtering. This is less preferred because in this case two filters would be required.

In case columns are used the stream is in this case divided before exposure to the sterol lipid in step ii), so that steps ii) and iv) can take place in the same column and step ii) and v) can take place in another column.

The substrate carrying an immobilised mycolic acid derived antigen and the substrate not carrying an immobilised mycolic acid derived antigen of steps iv) and v) are preferably of the same material.

In addition, since sterol lipids, (e.g. cholesterol) and mycolic acid derivatives are both hydrophobic, the substrates for exposure in steps iv) and v) may be of the same material as the substrate that may be used to in step ii). It will be understood that suitable substrate material is inert for non-specific binding of molecules of this sample.

The exposure time of the sample to the sterol lipid is preferably less than 10 minutes, such as 2 to 8, 3 to 7, 4 to 6 or about 5 minutes.

One exemplary way of exposing the sample to the substrates of step iv) and v) is to lead the divided sample streams into long spiral channels, preferably implemented in microchips, pre-coated either with a mycolic acid derivative (step iv) or without a mycolic acid derivative (step v) and pass it along the length of these channels.

An alternative exemplary way of exposing the divided lipid sterol exposed samples to a substrate coated either with a mycolic acid derivative or without a mycolic acid derivative is to inject the a first stream into a container comprising a substrate carrying an immobilised mycolic acid derived antigen (step iv), and a second sample stream into a container comprising a second substrate not carrying an immobilised mycolic acid derived antigen (step v) and incubate the samples for less than 10 minutes, such as 2 to 8, 3 to 7, 4 to 6 or about 5 minutes.

Another alternative way is that steps iv) and v) take place in a column. The stream is in this case divided before exposure to the sterol lipid in step ii), so that step ii) and iv) can take place in one column and step ii) and v) can take place in another column.

Although for reasons of reproducibility and reliability of the detection method it is preferred that in step v) said another fraction of the sterol lipid exposed sample is exposed to a substrate not carrying an immobilised mycolic acid derived antigen, it may also be possible that the step of exposing said fraction to a substrate not carrying an immobilised mycolic acid derived antigen is skipped and that said fraction is stored until further use, such as in step vi). This may for instance take place in the same column or container wherein the incubation with the sterol lipid took place.

Therefore, the invention also relates to a method which comprises the steps of:

i) providing a sample from a human or animal suspected of having active tuberculosis;

ii) contacting said sample to a sterol lipid;

iii) obtaining at least two fractions of said sample either before or after exposing it to said sterol lipid;

iv) exposing the first of said fractions to a substrate carrying an immobilised mycolic acid derived antigen;

v) storing at least part of the second of said fractions until step vi);

vi) exposing at least part of the sample fraction exposed in step iv) to a test substrate carrying an immobilised mycolic acid derived antigen and exposing at least part of the sample fraction stored in step v) to a control substrate carrying an immobilised mycolic acid derived antigen;

vii) detecting binding of antibodies to the antigen of step vi) in, an end-point assay; and viii) comparing the degree or extent of antibody binding between the test and control substrates, any observed lesser binding to the test substrate being an indicator of the presence of antibodies to the antigen in the sample that indicates active tuberculosis in the human or animal from which the sample originated.

In line with this, the invention also relates to a method for pre-treating a sample from a human or animal suspected of having active tuberculosis for detection:

i) providing a sample from a human or animal suspected of having active tuberculosis;

ii) exposing said sample to a sterol lipid;

iii) obtaining at least two fractions of said sample either before or after exposing it to said sterol lipid;

iv) exposing the first of said fractions to a substrate carrying an immobilised mycolic acid derived antigen;

v) storing of at least part of the second of said fractions for further use;

wherein after exposure in step iv) at least part of the exposed first sample fraction is stored for further use.

Step vi (End-Point Method)

In this step the divided sterol lipid exposed sample streams, either exposed to mycolic acid derivatives in step iv(test stream) or not in step v (control stream) are passed to further substrates, test and control substrates respectively, carrying mycolic acid derivatives, preferably the same derivatives as in step iv.

The test and control substrates may be any substrate which can carry an immobilized mycolic acid derivative antigen and from which binding between antibodies contained in the sample to said antigens can be detected.

In a preferred embodiment detection takes place by means of an immunogold filtration assay. In such an assay the test and control substrate are a microporous membrane, preferably a nitrocellulose membrane, which is coated an immobilised mycolic acid derived antigen.

The test substrate and the control substrate may be separate entities. Alternatively the test substrate and the control substrate may be realized as different positions on one substrate entity. For instance, in case of a microporous membrane the test substrate and the control substrate may be formed by a first microporous (e.g. nitrocellulose) membrane and a second microporous (e.g. nitrocellulose) membrane. Alternatively the test substrate and control substrate are contained on one membrane. In such a case there is a test area where antibody/antigen interaction can take place (e.g. a spot) on one position of the membrane and a control area where antibody/antigen interaction can take place on another position of the membrane.

Steps vii and viii (End-Point Method)

In step vii) the binding of antibodies to the immobilised mycolic acid antigens is detected in an end-point assay. At least part of the obtained pre-treated fractions is subjected to said end-point detection assay. It is possible to use the whole fractions for the end-point assay. Alternatively part of the fractions are used to detect binding of antibodies to the immobilised mycolic acid antigens in the end-point assay and another part is stored for further testing depending on the results of the first part of the fractions.

The term "end-point assay" is to be understood as an assay wherein the outcome of interest is the end result after a fixed assay incubation period, in contrast to a so-called real-time assay. In the context of the detection method of the invention that means that the treated samples obtained after steps iv) and v) are taken and subjected to a test that provides an indication of the amount of antibodies that are present in the treated samples after steps iv) and v).

An end-point detection assay may for instance detect changes to levels of color, fluorescence, absorbance or luminescence at the end of a test. In end-point assays detection may suitably be performed by means of techniques such as photospectroscopy, fluorescence microscopy, chemoluminescence or electrochemiluminescence detection techniques. This may involve use of for instance spectrophotometric/colorimetric plate readers, fluorescence plate readers or chemiluminescence readers.

Suitable end-point assays may involve enzyme-linked immunosorbent assay (ELISA), Western blotting, radioactive labelling assay, photospectrometric assay, immunofluorescence, immunoprecipitation, immunocytochemistry, immunohistochemistry, electrochemical impedance spectroscopy (EIS) etc. ELISA for instance involves at least one antibody with specificity for a particular antigen. In the context of the invention the antigen is a mycolic acid derived antigen and the antibody is an antibody against mycolic acid derivative antigens.

In an end-point assay interaction of antibodies with the mycolic acid derived antigens may be carried out using secondary antibodies that bind the heavy chain of the antibodies against the mycolic acid derivatives. Many suitable secondary antibodies are commercially available. The secondary antibody may be coupled to beads, for instance gold beads, or associated with liposomes. Examples of secondary antibodies may be protein A or G, possibly conjugated with an enzyme that enables detection.

A particular suitable technique or detecting the binding of antibodies to the immobilised mycolic acid antigens in step vii) is the so-called immunogold filtration assay (IGFA), and in particular the dot immunogold filtration assay (DIGFA).

Immunogold filtration assays are methods combining ELISA and immunogold technique and are methods in which a sample to be assayed is allowed to filtrate through a microporous membrane, preferably a nitrocellulose membrane, and is captured by a capture probe coated on the membrane. A colloidal gold labelled probe is allowed to filtrate through the microporous membrane in the same manner. By using a microporous membrane as the carrier for the capture probe and employing the capillary action and permeability of the membrane antigens and antibodies can easily react and may conveniently be subjected to optional washing and/or blocking steps. When the colloidal gold labelled probe binds to the capture probe the colloidal gold particles aggregate and a red dot appears which is visible with the naked eye.

Immunogold filtration assays are simple and rapid detection methods because no instruments are required except a membrane and the reagents and the results can be observed by the naked eye within a few minutes.

In an immunogold filtration assay the microporous membrane may be for example a nitrocellulose membrane, a cellulose acetate membrane or a PVDF membrane with a suitable pore diameter. Preferably nitrocellulose is used. A suitable pore diameter is 0.2 to 5 µm.

In the end-point method antibodies contained in a sample are detected by means of an end-point assay. In case the end-point assay is an immunogold filtration assay, the substrate mentioned in steps vi) and viii) of the detection method of the invention, is a microporous membrane, preferably a nitrocellulose membrane, which is coated an immobilised mycolic acid derived antigen. After immobilizing the mycolic acid derived antigen onto the microporous membrane, the sample fractions pre-treated in steps i) to v) can be applied to the membrane. After addition of the sample fractions and reaction of the immobilized mycolic acid derived antigens with the antibodies contained in the samples on the membrane, colloidal gold-labeled second antibodies are added onto the membrane to have gold particle aggregation in the antigen-antibody reaction place. In case of aggregation visible red or brown spots are formed. The intensity of the spot is proportional to the amount of reactions between antigen and antibody, i.e. to the amount of antibodies in the pre-treated sample. In case the control substrate shows a more intense signal than the test substrate this is indicative for active tuberculosis in the person from which the sample was derived. On the other hand, in case the control substrate shows no (or only insignificant) difference in color intensity signal compared the test substrate this indicates that the human or animal from which the sample was derived does not have active tuberculosis.

Between the various steps of an immunogold filtration assay the membrane may be washed with a suitable buffer, for example a PBS based buffer. Such buffer may for example be a PBS/AE buffer comprising NaCl, KCl, $KH_2PO_4$, $Na_2HPO_4$ and EDTA in water at physiological pH. Such buffer may be a PBS based buffer consisting of 8.0 g NaCl, 0.2 g KCl, 0.2 g $KH_2PO_4$, and 1.05 g $Na_2HPO_4$ per liter of double distilled, deionized water containing 1 mM EDTA and 0.025% (m/v) sodium azide which is adjusted to pH 7.4.

In case DIGFA is used, the microporous membrane may be coated with said mycolic acid derived antigen in a dot wise manner. In a DIGFA assay the samples pre-treated in steps i) to vi) are applied to the membrane in the form of dots. Also the colloidal gold-labeled second antibodies are added in the form of dots. In such an embodiment, the control and test substrate are preferably the same microporous membrane with dots of mycolic acid derived antigens immobilised thereon. The detection method of the invention makes it possible to detect both the control and test fractions on the same membrane. This improves reliability of the test and is cost effective. A DIGFA assay is particularly preferred because at different spots on several membranes various antigens deriving from various mycobacterial strains may be immobilized. This way it becomes possible to provide information on which mycobacterial strain a patient is infected with. Another advantage of using DIGFA is that samples derived from different persons suspected of having active tuberculosis can be compared in one test, because DIGFA enables fast and reliable detection of antibody-antigen interaction in an unlimited amount of spots, depending on the size of the membrane.

The detection of binding of antibodies and/or other material to the mycolic acid antigen, for instance the red staining in case a DIGFA assay is used as a detection method, may be carried out in an automated device. Various automated devices will be known to the person skilled in the art and the skilled person will be able to select suitable software means to make the comparison of step viii) of the degree or extent of binding between the test and control substrates, wherein any observed lesser binding to the test substrate is an indicator of the presence of antibodies to the antigen in the samples that relates to active tuberculosis in the human or animal from which the samples originated. In this context it should be understood that lesser can be interpreted qualitatively and quantitatively, i.e. lesser binding may be interpreted as having less binding events as well as having weaker bindings.

The detection of binding of antibodies and/or other material to the mycolic acid antigen may be performed by a visual detection technique or any other suitable detection technique. In a particular preferred embodiment, detection by means of the end-point assay takes place visually, preferably with the naked eye. This has the advantage of easy detection without the need for expensive and complicated detection technology.

In case DIGFA is used binding of antibody antibodies and/or other material to the mycolic acid antigen may be assessed by means of the naked eye.

A visual signal, e.g. the red staining in case a DIGFA assay is applied as end-point assay, may also be detected with help of a mobile app, i.e. a computer program designed to run on mobile devices such as tablet computers or smart phones. For instance, an app can be used that is designed to compare the binding signal of the test and control substrate and which indicates whether the human or animal from which the sample originated has active tuberculosis.

System

In another aspect the invention relates to a system or device, preferably a portable system or device, for carrying out an end-point method of detecting a marker for active tuberculosis. This system can be subdivided in 1) a system or device for pre-treating a sample stream from a human or animal suspected of having active tuberculosis in order to make the sample suitable for detection with the method of the invention; and 2) a detection means to enable detection of interaction of antibodies contained in the pre-treated sample.

In one embodiment the system comprises at least one container comprising a sterol lipid arranged and configured to receive a sample stream from a human or animal suspected of having active tuberculosis; means for dividing said sample stream into at least a first and a second sample stream; said means either connected upstream or downstream of said at least one container comprising a sterol lipid; a further container for receiving said first sample stream in downstream connection with a said container comprising a sterol lipid, and comprising a first substrate carrying an immobilised mycolic acid derived antigen; a still further container for receiving the second sample stream in parallel arrangement to said further container and in downstream connection with a said container comprising a sterol lipid; and comprising a second substrate not carrying an immobilised mycolic acid derived antigen, and a first detection substrate carrying an immobilised mycolic acid derived antigen to receive at least part of the first sample stream and a second detection substrate carrying an immobilised mycolic acid derived antigen to receive at least part of the second sample stream.

In a particular embodiment the system for carrying out a method of detecting a marker for active tuberculosis comprises at least one container comprising a sterol lipid arranged and configured to receive a sample stream from a human or animal suspected of having active tuberculosis; means for dividing said sample stream into at least a first and a second sample stream; said means either connected upstream or downstream of said at least one container comprising a sterol lipid; a further container for receiving said first sample stream in downstream connection with a said container comprising a sterol lipid, and comprising a first substrate carrying an immobilised mycolic acid derived antigen; a still further container for receiving the second sample stream in parallel arrangement to said further container and in downstream connection with a said container comprising a sterol lipid; and comprising a second substrate not carrying an immobilised mycolic acid derived antigen, and a first detection substrate carrying an immobilised mycolic acid derived antigen to receive at least part of the first sample stream from said further container and a second detection substrate carrying an immobilised mycolic acid derived antigen to receive at least part of the second sample stream from said still further container, wherein the first and second detection substrate are a microporous membrane.

The first and second detection substrates are preferably a microporous membrane, preferably a nitrocellulose membrane. The first and second detection substrates may in this case have separate spots, i.e. first and second detection spots, on the same membrane. This way one and the same membrane can be used for detection of antibody/antigen interaction. This increases reliability of the detection and makes it easier to compare the interaction detected on the test and control substrate. Moreover, this enables multiple samples to be tested at the same time.

The detection Substrates do not have to be in physical connection with the other components of the system. For instance the samples derived after passing said further and still further containers may be stored until further use or for transport to the detection substrate. This way the practicer has great flexibility in planning his test. For instance, this allows pre-treated samples from a number of subjects to be collected, so that they can be tested all at once on one substrate material. This also makes it easier to test samples from multiple patients under the same conditions.

Therefore, in another aspect the invention relates to a system or device, preferably a portable system or device, for pretreating a sample stream from a human or animal suspected of having active tuberculosis in order to make the sample suitable for detection in a detection method, comprising at least one container comprising a sterol lipid arranged and configured to receive a sample stream from a human or animal suspected of having active tuberculosis; means for dividing said sample stream into at least a first and a second sample stream; said means either connected upstream or downstream of said at least one container comprising a sterol lipid; a further container for receiving said first sample stream in downstream connection with a said container comprising a sterol lipid, and comprising a first substrate carrying an immobilised mycolic acid derived antigen; a still further container for receiving the second sample stream in parallel arrangement to said further container and in downstream connection with a said container comprising a sterol lipid; and comprising a second substrate not carrying an immobilised mycolic acid derived antigen, and a means for storage or transport of the treated samples. This or these means do not have to be in physical connection with the containers comprising said first and second substrates respectively and are located downstream of these containers when the system is in use in order to receive the pre-treated sample fractions.

In one embodiment the system or device for pre-treating a sample stream from a human or animal suspected of having active tuberculosis in order to make the sample suitable for detection with the method of the invention may comprise two columns. Each column comprises two compartments or containers. An upper compartment or container comprises a substrate coated with a sterol lipid, for instance beads coated with cholesterol. A lower compartment of one of the columns comprises a first substrate carrying an immobilised mycolic acid derived antigen and a lower compartment of another column comprises a substrate not carrying an immobilised mycolic acid derived antigen.

In this respect the invention also relates to a system for pre-treating a sample stream derived from a human or animal suspected of having active tuberculosis, which comprises means for dividing said sample stream into at least a first and a second sample stream; at least a first and a second column, configured to receive said first and a second sample stream respectively; said first column comprising a compartment comprising a sterol lipid and a further compartment comprising a first substrate carrying an immobilised mycolic acid derived antigen downstream of said compartment comprising a sterol lipid; and said second column comprising a compartment comprising a sterol lipid and a still further compartment comprising a second substrate not carrying an immobilised mycolic acid derived antigen downstream of said compartment comprising a sterol lipid; and means for storage or transport of the treated samples passed through said columns. This or these means for storage and transport do not have to be in physical connection with the containers comprising said first and second substrates respectively and are located downstream of the columns when the system is in use in order to receive the pre-treated sample fractions.

This principle can also be applied to a system for carrying out an end-point method of detecting a marker for active tuberculosis. In this respect the invention also relates to a system for carrying out a method of detecting a marker for active tuberculosis in a sample derived from a human or animal suspected of having active tuberculosis, which comprises means for dividing said sample stream into at least a first and a second sample stream; at least a first and a second column, configured to receive said first and a second sample stream respectively; said first column comprising a compartment comprising a sterol lipid and a further compartment comprising a first substrate carrying an immobilised mycolic acid derived antigen downstream of said compartment comprising a sterol lipid; and said second column comprising a compartment comprising a sterol lipid and a still further compartment comprising a second substrate not carrying an immobilised mycolic acid derived antigen downstream of said compartment comprising a sterol lipid and a first detection substrate carrying an immobilised mycolic acid derived antigen to receive at least part of the first sample stream and a second detection substrate carrying an immobilised mycolic acid derived antigen to receive at least part of the second sample stream.

Preferably the system or device comprises a skin penetrating end connected to a first tubing, which is arranged and configured receive a blood sample from the skin penetrating end and to carry said blood sample away from the skin site to said container/compartment comprising a sterol lipid.

In another preferred embodiment the system or device comprises a filter unit in connection with said first tubing for receiving said blood sample and configured to separate plasma from said whole blood sample.

In a further embodiment the system or device comprises a skin penetrating end connected to a first tubing, which is arranged and configured receive a blood sample from the skin penetrating end and to carry said blood sample away from the skin site; a filter unit in connection with said first tubing for receiving said blood sample and configured to separate plasma from said whole blood sample; a first container for receiving said sample, said first container comprising a sterol lipid; means for dividing said sample into at least a first and a second sample stream; a second container for receiving said first sample stream, said second container comprising a first substrate carrying an immobilised mycolic acid derived antigen; a third container for receiving the second sample stream, said third container comprising a second substrate not carrying an immobilised mycolic acid derived antigen; and a means for storage or transport of the treated samples.

The stream through the system or device is preferably driven by a pump, preferably a continuous flow pump, for example a peristaltic pump or a diaphragm pump. In case columns are applied, the stream may be driven by gravity or capillary action The skin penetrating means may be any suitable means to obtain a blood sample from a human or animal, such as a needle syringe or the like.

The first tubing has dimensions that are suitable for purpose of the device, i.e. it needs to be well adaptable to the skin penetrating means and the first container.

The components of the system or device, i.e. the containers, means for diluting and filter unit may be interconnected by suitable interlinking tubings. Alternatively the components of the device may be designed such that they can be connected directly to each other, and separated by for instance filters through which the sample but not the substrate can selectively pass. The material of the tubings used in the invention can be any suitable material which is known to the person skilled in the field of testing blood samples. Suitable materials are inert to blood/plasma/serum components and include polytetrafluorethylene (e.g. Teflon®), polypropylene, polyetherketone (PEEK) and polyethylene.

Further components may be connected between the components of the device. Such further components may be connected in tubings interlinking the components are directly attached to the components.

The system or sub-device for performing steps i-v of the methods of the invention may also comprise a means for dilution of the blood or plasma. Such means may be implemented before the sterol lipid containing container, before the filter unit, between the filter unit and the sterol lipid containing container, between the sterol containing container and the other (further and still further or (second and third) containers or between the further/still further or second/third containers and the means for storage and transport. For instance a 10 ml container may be implemented at the outlet of the further or second and still further or third containers. A suitable buffer may already be present in the container or be added into this container to provide the desired dilution. This way the volume of the sample is kept as low as possible during most of the steps of the methods of the invention, which is beneficial to the speed of the process and the compactness of the device of the invention.

The filter unit may comprise a filter matrix. Preferably the filter is implemented on a filter microchip for the sake of compactness.

The containers may be vessels or a channel, or tubing, such as a spiral channel or spiral tube. A spiral channel or tube is preferred because such structure takes little space whilst maintaining a long flow path. A spiral channel or tube may be advantageously implemented on a micro-chip. This contributes to the compactness of the device of the invention. The term "container" is to be interpreted in the broad sense, i.e. it can be seen as defined area in another unit, i.e. a compartment, for instance a compartment of a column. The terms "container" and "compartment" may thus be used interchangeably in the context of the present invention. What matters is that sterol lipid containing container and the other (further and still further or (second and third) containers are spatially separated. In this respect a sterol containing container may be included in a column together with said further (or second) container while another sterol containing container is included in a column together with a still further (or third) container. In the context of the invention a column for preparing a stream to be tested on a test substrate may comprise an upper (or upstream) substrate coated with a sterol lipid which is separated by a barrier from, but in fluid connection with a lower (or downstream) substrate coated with mycolic acid derived antigens. A column for preparing a stream to be tested on a control substrate may comprise an upper (or upstream) substrate coated with a sterol lipid which is separated by a barrier from, but in fluid connection with a lower (or downstream substrate not coated with mycolic acid derived antigens. It is to be understood that in connection in this context means that the sample to be tested can pass through said barrier, while the barrier does not allow passing of the substrates. Suitable substrates for such columns are beads. In this respect an embodiment of the system of the invention for pre-treating a sample stream from a human or animal suspected of having active tuberculosis in order to make the sample suitable for detection with the method of the invention comprises at least a first and a second column, configured to receive said first and a second sample stream respectively, said first column comprising a container comprising a sterol lipid and said further container comprising a first substrate carrying an immobilised mycolic acid derived antigen, and said second column comprising a container comprising a sterol lipid and said still further container comprising a second substrate not carrying an immobilised mycolic acid derived antigen.

The material of the containers is preferably the same and suitable materials may be bk-7 glass, polytetrafluorethylene, polypropylene, polyether ketone or polyethylene. A boundary between two containers may be a filter that does not allow substrate material to pass, but which does allow passage of a sample stream. The substrates of the containers have to be material that is inert for non-specific binding of molecules of the sample, for instance bk-7 glass, polytetrafluorethylene, polypropylene, polystyrene polyether ketone or polyethylene. The substrates may be in the form of beads, optionally crosslinked beads, for instance polystyrene beads.

The systems of the invention comprise a container comprising a substrate carrying an immobilised mycolic acid derived antigen (second container) and a container comprising a substrate not carrying an immobilised mycolic acid derived antigen. Instead of an immobilised mycolic acid derived antigen, the latter container may an inert coating or no coating, as long as no a specific binding takes place.

The means for storage or transport of the treated samples may be small vials wherein the samples are stored for further analysis, for example by means of a dot immunogold filtration assay. Alternatively, the means may be formed by a pipette which can be applied to transfer the sample fractions treated in steps i)-v) of the methods of the invention to the substrates with immobilised mycolic acid derived antigens of the end-point assay, for instance to spot fractions as dots in a dot immunogold filtration assay.

The device/system may be connected to any suitable automated analysis means, such as a computer with suitable software programs to carry out the comparison of binding of mycolic acid antibodies to the immobilised antigens on the substrate.

An exemplary embodiment of the system according to claims 10 and 11 is shown in FIG. 2.

FIG. 2 shows a skin penetrating needle 1 connected to a first tubing 102, which is arranged and configured receive blood from the needle 101 and to carry the amount of blood away from the skin site. Tubing 101 is connected to a filter unit 103. This filter unit serves to separating plasma from said whole blood sample. Filter unit 103 is connected via tubing 113 to a first container 14, which is in the form of a spiral channel of which the inner wall is coated with a sterol lipid. The spiral channel is connected via tubing 114 with a means for dividing plasma 105 in the form of a passive valved branch point. One branch of the branch point is connected via tubing 116 with a second container 106 for receiving a first plasma stream, which comprises a first substrate carrying an immobilised mycolic acid derived antigen. The other branch of the branch point is connected via tubing 115 with a third container 107 for receiving a second plasma stream, which comprises a second substrate not carrying an immobilised mycolic acid derived antigen. Containers 106 and 107 in this embodiment are in the of a spiral channel of which the inner wall is either coated with a mycolic acid derived antigen (container 106) or not coated with a mycolic acid derived antigen (container 107). Containers 106 and 107 are connected via respectively tubings 117 and 118 with dilution containers 111 and 112 respectively. These containers may be prefilled with a suitable dilution buffer of comprise inlets 121, 122 for introducing a dilution buffer. The dilution containers 121 and 122 can be connected via respective tubings 119 and 120 to means for storage or transport 108 and 109 respectively. Alternatively, the dilution containers 121 and 122 can be connected via respective tubings 119 and 120 to test and control substrates with immobilized mycolic acid derived antigens that are tested in an end-point assay.

Kit

In another aspect the invention relates to a kit for use in diagnosing tuberculosis or pre-treatment of samples for diagnosing tuberculosis, comprising one or more skin penetrating means; one or more tubings; one or more containers coated with a sterol lipid and optionally phosphatidyl choline, pectin, amphothericin B or β-cyclodextrin; one or more containers comprising a substrate with an immobilised mycolic acid derived antigen; one or more containers comprising a substrate without an immobilised mycolic acid derived antigen; optionally one or more containers for transport and storage of samples; optionally means for diluting blood or plasma and/or a filter unit; at least one microporous membrane with mycolic acid derived antigen immobilised thereon, and optionally secondary antibodies binding to the heavy chain of antibodies against mycolic acid derived antigens contained in a sample derived from a human or animal suspected of having active tuberculosis, preferably colloidal gold-labelled second antibodies.

In a preferred embodiment the kit comprises: one or more skin penetrating means; one or more tubings; one or more columns, comprising a compartment comprising a substrate coated with a sterol lipid and optionally phosphatidyl choline, pectin, amphothericin B or β-cyclodextrin; and a compartment comprising a substrate coated with an immobilised mycolic acid derived antigen below said compartment comprising a substrate coated with a sterol lipid; one or more columns, comprising a compartment comprising a substrate coated with a sterol lipid and optionally phosphatidyl choline, pectin, amphothericin B or β-cyclodextrin; and a compartment comprising a substrate coated without an immobilised mycolic acid derived antigen below said compartment comprising a substrate coated with a sterol lipid, optionally one or more containers for transport and storage of samples; optionally means for diluting blood or plasma and/or a filter unit; optionally at least one microporous membrane with mycolic acid derived antigen immobilised thereon, and optionally secondary antibodies binding to the heavy chain of antibodies against mycolic acid derived antigens contained in a sample derived from a human or animal suspected of having active tuberculosis.

The kit may also comprise one or more means to transfer sample fractions pre-treated in accordance with steps i) to v) of the methods of the invention to the microporous membrane, for instance a pipette and pipette accessories, such as pipette tips.

The kit may also comprise one or more means to store sample fractions pre-treated in accordance with steps i) to v) for further use, such as vials or tubes.

The kit may also comprise tools to assemble the components, such as screws, clamps, glue, tape, screwdrivers etc.

The kit may also comprise means to dilute the blood or plasma during blood analysis, such as containers (for instance of 10 ml) which can be implemented at the outlet of the second and third containers. A suitable buffer may already be present in the container or be added into this container to provide the desired dilution.

The components of the kit enable the person that is to perform a tuberculosis diagnosis test to assemble the systems of the invention on the spot, i.e. at the point of care. It is therefore to be understood that the components of the kit have the same characteristics and preferred properties as explained above for the systems of the invention. The systems of the invention are easy to be assembled by means of the components of the kit of the invention, i.e. no specialist technical background is required. The kit may be provided conveniently with instructions for assembly and use.

Sterol Lipids

The sterol lipid used in the context of the invention preferably is cholesterol or a derivative thereof. The sterol lipid may also be a sterol modified phospholipid. Such sterol-modified lipid may a sterol-modified phospholipid, for instance a sterol-modified phosphatidylcholine lipid or glycerophospholipid. In such sterol modified lipid the sterol is preferably cholesterol. A good example of a sterol-modified lipid suitable for the purposes of the invention is 1-palmitoyl-2-cholesteryl carbonoyl-sn-glycero-3-phosphocholine.

The sterol lipid is preferably immobilized on a surface. An example is a substrate having a coating containing cholesterol or cholesterol ester wherein the cholesterol ester is cholesterol linoleate, wherein a weight ratio of linoleic acid to cholesterol is in the range from 1:3 to 1:20.

A substrate may also be coated with a sterol lipid, preferably cholesterol, in combination with other molecules.

Preferably said sterol lipid is cholesterol immobilized on a substrate together with phosphatidyl choline. The sterol lipid scavenges away the anti-cholesterol antibodies from the blood/plasma/serum that would otherwise cross react with the mycolic acid antigens on the substrate and lead to false positive diagnosis of tuberculosis. Phosphatidyl choline will bind to hydrophobic materials in the blood sample, rendering the sample more hydrophilic after exposure. The resulting hydrophilic sample will easier to be handled in the subsequent method steps and be less prone to clotting.

In one embodiment a sterol lipid, preferably cholesterol is immobilised in together with pectin on a substrate, e.g. the inner wall of a tubing. In this embodiment the sterol lipid scavenges away the anti-cholesterol antibodies from the blood/plasma/serum that would otherwise cross react with the mycolic acid antigens on the substrate and lead to false positive diagnosis of tuberculosis. In addition pectin scavenges away cholesterol in the sample and therewith also cholesterol antibodies. This leads to an even higher reliability of detection.

Alternatively a sterol lipid, preferably cholesterol is immobilised together with a compound binding to cholesterol in the blood derived sample, such as cholesterol binding heteropolysaccharide, such as β-cyclodextrin, pectin, amphotericin B or dextrin. Such molecules scavenge away cholesterol in the sample and therewith also cholesterol antibodies. This leads to an even higher reliability of detection.

For instance a sterol lipid, preferably cholesterol is immobilised with β-cyclodextrin or pectin, amphotericin B on a substrate, such as hollow fiber polypropylene membranes or glass.

Many methods are known to immobilise a sterol lipid, in particularly cholesterol on a substrate. The skilled person will be able to select the protocol suitable for his particular coating. For example a coating may be applied by initially dissolving cholesterol in an organic solvent and further diluting the dissolved cholesterol in an ethanol solution, permitting the solution to evaporate in place within a container, rinsing the coated container with buffered saline, air-drying the container, and sealing the container in vapor-proof pouches with desiccant.

Mycolic Acid Derived Antigens

The mycolic acid derived antigen may be derived from mycobacteria selected from virulent and pathogenic mycobacteria. Preferably, the mycolic acid antigen is derived from *Mycobacterium tuberculosis*. Said mycolic acid derived antigen is at least one selected from the group of mycolic acid, cord factor, chemically modified mycolic acid, chemically modified cord factor, a synthetic mycolic acid derivative, a synthetic cord factor derivative.

Natural sources of mycolic acid derivatives include the cell walls of mycobacteria such as *Mycobacterium* tuberculosis include mixtures of different classes of compounds and different mycolic acid homologues, often as derivatives in which they are bonded to the wall of the cell.

In addition to the mycolic acids themselves, the cells of mycobacteria also contain compounds derived from the acid, such as sugar esters of mycolic acids. Naturally occurring sugar esters comprise for instance trehalose-6,6'-dimycolate, commonly referred to as TDM, also known as "cord factors"; and trehalose monomycolates (often referred to as TMM). These sugar esters occur in nature as complex mixtures of different classes of mycolic acids and of different homologues within each class.

Because it is difficult to establish the identity of cord factors present in natural products and to separate individual molecular species it is preferred to use semi-synthetic or more preferably synthetic mycolic acid derivatives for the purposes of the invention. Further, it is known that the structure of the mycolic acid unit affects the biological activity of the cord factor. Therefore when natural mycolic acid derivatives would be used in the present invention the difference in biological activity between these derivatives and thus the detection of binding of antibodies of the antigen in the sample may impart a factor of unpredictability and uncertainty to the outcome of the detection. In addition, deviations in the preparation of the natural mycolic acid derivatives may result in problems regarding reproducibility of different test batches.

Therefore in order to be able to provide a detection with high reliability and reproducible results it is preferred to use semi-synthetic or even more preferred synthetic mycolic acid derivatives which are identical or closely analogous to single compounds found in natural mixtures.

Suitable semi-synthetic derivatives include semi-synthetic cord-factors which may be prepared by attaching mycolic acids to the sugar group. These semi-synthetic factors however still contain mixtures of different homologue.

Therefore particular suitable mycolic acid derivatives for use in the context of the present invention are synthetic cord factors, for example the synthetic cord factors described in WO 2010/08667, i.e. compounds of formula $(M)_x (S)_y (M')_z$, wherein x is from 1 to 6, y is from 1 to 12, z is from 0 to 10, each M and each M' is independently a mycolic acid residue including a β-hydroxy acid moiety and each S is a monosaccharide unit.

The mycolic acid antigen may be in a form selected from homogenous and heterogeneous compound mixtures. The mycolic acid derived antigen may for instance be used in combination with a phospholipid such as phosphatidylcholine.

The mycolic acid antigen may be immobilised on the substrates in various ways that are known to the skilled person. Synthetic mycolic acid derived antigens may be synthesised with particular active groups that enable immobilisation to a substrate material.

For instance, for immobilisation on silica, silane coupling chemistry may be applied.

In case of a nitrocellulose substrate the mycolic acid derived antigen may be suitably immobilised as follows. Mycolic acid derived antigens may be obtained in lyophilized form and be reconstituted in a solvent mixture, for instance a chloroform: methanol: water mixture, and diluted to a concentration in the order of several nanomolars, for instance 1 nM. This dilution can then be spotted on a nitrocellulose membrane, wherein each spot is separated at a predetermined distance, e.g. 1 cm. After drying of the spots the mycolic acid derived antigens are immobilized on the membrane. Alternative immobilisation methods may for instance involve dissolving the antigens in hexane or hot PBS to form an antigen coating solution before spotting the solution on a membrane.

Examples

The following example is meant to illustrate the principle of the invention and should not be interpreted as limiting the scope of the claims. In the example a human serum sample was tested for antibodies against mycolic acid derivatives in an ELISA assay. As a detection method an ELISA method was chosen because it is less sensitive than for example Surface Plasmon Resonance or electrochemical impedance spectroscopy (EIS) or Ring Resonance (Interferometry). Therefore it can be concluded that if satisfactory results are obtained with ELISA, these will also be obtained with more sensitive detection methods.

Materials:
  Sample (human plasma or serum)
  0.2 micron spinfilters (Whatman)
  Mycolic Acid and Cholesterol-coupled beads
  polyclonal Mycolic Acid dissolved in hexane
  Polystyrene ELISA plates
  PBS
  Blocking buffer: 0.5% casein in PBS
  1-step ultra TMB-ELISA substrate solution
  (Thermo Scientific)
  2M sulfuric acid
  Secondary antibody: rabbit anti-human Ig HRP (DAKO)
Procedures
  Coating of ELISA Plates To each well of 96-wells ELISA plates 50 µl (of hexane with polyclonal mycolic acid in a concentration of 3 µg/ml was added. Hexane without mycolic acid was used as control. Plates were incubated for 24 hrs at 4° C. and subsequently washed two times with PBS.

Preparation of the Beads

In the present example beads were used as a substrate representative of the substrate mentioned in steps ii), iv and v) of the methods of the invention.

For purpose of this example Toyopearl AF-Amino-650M beads (Tosoh Bioscience) were used. Beads were prepared in accordance with the manufacturer's instructions. As cholesterol 7-keto cholesterol was conjugated to the beads basically as described in Abdel-Magid A F et al. (Reductive Amination of Aldehydes and Ketones with Sodium Triacetoxyborohydride. Studies on Direct and Indirect Reductive Amination Procedures. J. Org. Chem. 1996:61; 3849-3862) by mixing 7-keto cholesterol (100 mg, 0.25 mmol) and Toyopearl slurry (2.5 ml, 0.25 mmol reactive groups) in acetonitrile (3.5 ml), followed by treating with sodium triacetoxyborohydride (80 mg, 0,375 mmol). The mixture was stirred at RT under a $N_2$ atmosphere for 1.5 h. After that, the reaction mixture was quenched by adding aqueous saturated $NaHCO_3$. The beads were washed thoroughly with $H_2O$, 1M NaCl, and finally $H_2O$ to remove excess ligand. After that the residual amino groups were acetylated by adding 8 ml of 0.2M sodium acetate and 4 ml of acetic anhydride to the resin at 0° C. for 30 minutes followed by adding another 4 ml of acetic anhydride and incubation at 25° C. for 30 minutes.

As mycolic acids a mixture of natural occurring isoforms of mycolic acid (Mw ~1100-1300) was used to be coupled to the beads basically as described in Law B, Jenner WN. Immunoassay: A Practical Guide. London: Taylor & Francis. 2005: p 11-31 and Hermanson G T. Bioconjugate Techniques. 3th ed. London; Elsevier. 2013: p 535-545. In short, N-(3-Dimethylaminopropyl)-N'-ethylcarbodiimide hydrochloride (EDC.HCl) (57.7 mg, 0.3 mmol (1.2 equiv.)) and N,N-diisopropylethylamine (DIPEA) (81.3 mg, 0,625 mmol (2.5 equiv.)) were added to a solution of amine (Toyopearl amino-activated, 2.5 mL, 0.25 mmol reactive groups), acid (isolithocholic acid: 93.8 mg, 0.25 mmol (1 equiv.)/Mycolic acids: 300 mg, 0.25 mmol (1 equiv.)) and HOBt (1-Hydroxybenzotriazole hydrate) (40.5 mg, 0.3 mmol (1.2 equiv.)) in DMF (2.5 mL (10 ml/1 mmol)) and stirred/shaken for 24 hours at room temperature under nitrogen. The solvent was removed by evaporation and the beads were washed used water and 1M NaCl and water. Excess (unbound) amino groups were blocked using acetylation. Beads were washed using water, 1M NaCl and water. First an inert atmosphere with nitrogen or argon is created. The order of the reagents: Mycolic acids with DMF (at 0° C.), then (HOBt), 10 min later beads, 10 min later base (DIPEA) and finally 15 min later EDC.

Sample Preparation

Serum derived from a human that were known to be suffering of tuberculosis was diluted 1:5 in blocking buffer. The samples used were derived from both smear positive and smear negative patients. Two fractions of 0.5 ml were obtained and transferred each to a 0.2 micron spin filter and centrifuged at 10000 g. The flow-through was pooled from 1:5 to 1:20 in blocking buffer.

250 µl of the flow-through was added to beads which were either coated with cholesterol, polyclonal mycolic acids or blocking agent. Beads were agitated at room temperature. After incubation the beads were spun down fast and the supernatant was used as a sample. The total pre-treatment of the samples with beads (in line with steps i)-v) of the method(s) of the invention in this particular set up may take place in less than 10 minutes, after which analysis can directly follow.

ELISA-Procedure

To block a specific binding of antibodies with the mycolic acids in the wells of the ELISA plates, 300 µl of blocking buffer was added to each well and incubated for 1 hour. Subsequently, the blocking buffer was replaced with 45 µl of sample. Blocking buffer was used as a negative control. After incubation, the plates were washed three times with PBS. The washing PBS buffer was replaced with HRP-conjugated secondary antibody in blocking buffer. After incubation, the plate was washed again three times with PBS. Subsequently 50 µl per well of TMB-ELISA substrate solution was added to the wells and incubated for 15-30 min at room temperature. The reaction was stopped by adding 50 µl per well of 2 M sulphuric acid. Absorbance at 450 nm was measured to quantify the binding of antibodies to the mycolic acid substrate of the ELISA plate.

Treatment of Samples

Samples were treated as follows.

1. In a first comparing study, two fractions (1 and 2) were taken from each of 6 samples derived from different humans. All fractions were separately incubated with beads without any agent coupled (fraction 1 and 2) and stored until ELISA detection. The average ELISA signal obtained from each fraction determined. Both fractions had the same results. The ELISA signal of these two fractions was set at 100%.

2. In a second comparing study, two fractions (3 and 4) were taken from each of the abovementioned 6 samples. The samples of fraction 3 were separately incubated with beads coupled with only blocking agent and subsequently stored until ELISA detection. The samples of fraction 4 were separately incubated with beads coupled with cholesterol and subsequently stored until ELISA detection.

3. In a third comparing study, two fractions (5 and 6) were taken from each of the abovementioned 6 samples. The samples of fraction 5 were separately incubated with beads coupled with cholesterol and subsequently stored until ELISA detection. The samples of fraction 6 were first separately incubated with beads coupled with cholesterol, subsequently the samples were spun of fast and the supernatant was used for a second incubation with beads coupled with polyclonal mycolic acid. Samples were subsequently stored until ELISA detection.

4. In a further study, two fractions (7 and 8) were taken from each of the abovementioned 6 samples. Both fractions 7 and 8 were incubated with beads coupled with cholesterol and beads as a substrate coupled with polyclonal mycolic acid simultaneously and subsequently stored until ELISA detection.

Except for differences in beads all other conditions were the same for all treatments.

Results

The average ELISA signal obtained from each fraction of the 6 samples was determined. The ELISA signal of fractions 1 and 2 was the same and was set at 100%. The ELISA signal of the other fractions is shown in percentages of the signal of fraction 1 (or 2) in Table I below.

TABLE I

ELISA results

| Fraction | ELISA signal |
| --- | --- |
| Fraction 1 | 100% |
| Fraction 2 | 100% |
| Fraction 3 | 81% |
| Fraction 4 | 68% |
| Fraction 5 | 73% |
| Fraction 6 | 54% |
| Fraction 7 | 96% |
| Fraction 8 | 96% |

These results show that samples that are exposed first to a sterol lipid and subsequently to a substrate carrying an immobilised mycolic acid derived antigen (the samples of fraction 6) have lower ELISA signal than any of the other fractions tested. A clear difference can be seen between fractions 5 and 6, which comparing study can be seen as an exemplary embodiment of the end-point method of detecting a marker for active tuberculosis according to the invention. Surprisingly the low ELISA signal obtained from fraction 6 cannot be obtained by incubating a sample with beads coupled with cholesterol and beads coupled with polyclonal mycolic acid simultaneously. In fact, the ELISA signals of fractions 7 and 8 are even higher than the ELISA signal of beads coupled with blocking agent alone or beads coupled with cholesterol. Also no satisfactory results were obtained when a fraction was exposed to beads coupled with mycolic acid alone. From this, it appears that it is important that pre-treatment of a sample takes place in two subsequent steps of 1) exposure to a sterol lipid and 2) exposure to a mycolic acid derivative to obtain the most marked decrease in signal and therefore antibody binding compared to a control sample which has not been exposed to a mycolic acid derivative.

Further, from the example it follows that the total pre-treatment of the samples with beads (in line with steps i)-v) of the method(s) of the invention) in this particular set-up can take place in less than 10 minutes, after which analysis can directly follow.

The time that is required for analysis is dependent on the detection assay that is applied. As mentioned above, instead of analysis with ELISA, other detection assays are possible. The samples pretreated as described above, can be analyzed using any suitable label free technology. The inventor has found in particular that when electrochemical impedance spectroscopy (EIS) is applied detection of binding of antibodies present in the samples to the detection substrates can take place within seconds. This makes it possible to determine whether or not an individual is infected with active tuberculosis in a fast and reliable way, allowing detection of tuberculosis in less than 10 minutes.

The invention claimed is:

1. A method of detecting a marker for active tuberculosis, consisting essentially of the steps of:

i) providing a sample from a human or animal suspected of having active tuberculosis;

ii) scavenging away anti-cholesterol antibodies from the sample by exposing said sample to a sterol lipid immobilised on a substrate, wherein said sterol lipid is cholesterol or a derivative thereof;

iii) obtaining at least two fractions of said sample either before or after exposing said sample to said sterol lipid;

iv) exposing a first of said sterol lipid exposed fractions to a substrate carrying an immobilised mycolic acid derived antigen;

v) exposing a second of said sterol lipid exposed fractions to a substrate not carrying an immobilised mycolic acid derived antigen; or storing at least part of the second of said fractions until step vi), skipping the step of exposing the second of said fractions to a substrate not carrying an immobilised mycolic acid derived antigen;

vi) exposing at least part of the sample fraction exposed in step iv) to a test substrate carrying an immobilised mycolic acid derived antigen and exposing at least part of the sample fraction exposed or stored in step v) to a control substrate carrying an immobilised mycolic acid derived antigen;

vii) detecting binding of antibodies to the antigen of step vi) in an end-point assay; and viii) comparing a degree or extent of binding between the test and control substrates, wherein any observed lesser binding to the test substrate being an indicator of the presence of antibodies to the antigen in the sample that indicates active tuberculosis in the human or animal from which the samples originated; and wherein prior to step vi), the test and control substrate of step vi) have not been preincubated with a dilution of said sample derived from a human or animal suspected of having active tuberculosis.

2. The method according to claim 1, wherein the endpoint assay is selected from the group consisting of enzyme-linked immunosorbent assay (ELISA), Western blotting, radioactive labelling assay, photospectrometric assay, immunofluorescence, immunoprecipitation, immunocytochemistry, immunohistochemistry, electrochemical impedance spectroscopy, an immunogold filtration assay, or a dot immunogold assay (DIGFA).

3. The method according to claim 1, wherein detection leads to a visual signal which is analysed using a mobile app that is designed to compare a binding signal of the test and control substrates and which indicates whether the human or animal from which the sample originated has active tuberculosis.

4. A method for pre-treating a sample from a human or animal suspected of having active tuberculosis for detection according to the method of claim 1, consisting essentially of the steps of:
   i) providing a sample from a human or animal suspected of having active tuberculosis;
   ii) scavenging away anti-cholesterol antibodies from the sample by exposing said sample to a sterol lipid immobilised on a substrate, wherein said sterol lipid is cholesterol or a derivative thereof;
   iii) obtaining at least two fractions of said sample either before or after exposing said sample to said sterol lipid;
   iv) exposing the first of said sterol lipid exposed fractions to a substrate carrying an immobilised mycolic acid derived antigen; and
   v) exposing the second of said sterol lipid exposed fractions to a substrate not carrying an immobilised mycolic acid derived antigen; or storing of at least part of the second of said fractions for further use, skipping the step of exposing the second of said fractions to a substrate not carrying an immobilised mycolic acid derived antigen;
   wherein after exposure in steps iv) and v) at least part of the exposed sample fractions are stored for further use.

5. A system for detecting a marker for active tuberculosis according to the method of claim 1, comprising at least one container comprising a sterol lipid immobilised on a substrate, wherein said sterol lipid is cholesterol or a derivative thereof arranged and configured to receive a sample stream from a human or animal suspected of having active tuberculosis; a splitter for dividing said sample stream into at least a first and a second sample stream; said splitter either connected upstream or downstream of said at least one container comprising said sterol lipid; a further container for receiving said first sample stream in downstream connection with a said container comprising said sterol lipid, and comprising a first substrate carrying an immobilised mycolic acid derived antigen; a still further container for receiving the second sample stream in parallel arrangement to said further container and in downstream connection with a said container comprising said sterol lipid; and comprising a second substrate not carrying an immobilised mycolic acid derived antigen, and a first detection substrate carrying an immobilised mycolic acid derived antigen to receive at least part of the first sample stream from said further container and a second detection substrate carrying an immobilised mycolic acid derived antigen to receive at least part of the second sample stream from said still further container.

6. The system according to claim 5, further comprising a biosensor comprising a first chamber for receiving the first sample stream in connection with said further container, comprising a substrate carrying an immobilised mycolic acid derived antigen, and a second chamber for receiving the second sample stream in connection with said still further container and comprising the same substrate carrying an immobilised mycolic acid derived antigen as the first chamber.

7. The system according to claim 5, further comprising a filter unit in connection with said first tubing and said first container and configured to separate plasma from a whole blood sample, preferably
wherein the filter unit comprises a filter matrix.

8. The system according to claim 5, comprising
   a skin penetrating end connected to a first tubing, which is arranged and configured receive a blood sample from the skin penetrating end and to carry said blood sample away from the skin site;
   a filter unit in connection with said first tubing for receiving said blood sample and configured to separate plasma from said whole blood sample;
   a first container for receiving said sample, said first container comprising said sterol lipid;
   a splitter for dividing said sample into at least a first and a second sample stream;
   a second container for receiving said first sample stream, said second container comprising a first substrate carrying an immobilised mycolic acid derived antigen;
   a third container for receiving the second sample stream, said third container comprising a second substrate not carrying an immobilised mycolic acid derived antigen; and
   a biosensor comprising a first chamber for receiving the first sample stream in connection with the second container, comprising a substrate carrying an immobilised mycolic acid derived antigen, and a second chamber for receiving the second sample stream in connection with the third container and comprising the same substrate carrying an immobilised mycolic acid derived antigen as the first chamber.

9. The system according to claim 5, wherein the substrate of the first and second chambers is silica based, preferably, wherein said biosensor comprises a Si ring resonator.

10. A system for pre-treating a sample stream from a human or animal suspected of having active tuberculosis for use in the method of claim 1, comprising at least one container comprising a sterol lipid immobilized on a substrate, wherein said sterol lipid is cholesterol or a derivative thereof, arranged and configured to receive said sample stream cholesterol; a splitter for dividing said sample stream into at least a first and a second sample stream; said splitter either connected upstream or downstream of said at least one container comprising said sterol lipid; a further container for receiving said first sample stream in downstream connection with a said container comprising said sterol lipid, and comprising a first substrate carrying an immobilised mycolic acid derived antigen; a still further container for receiving the second sample stream in parallel arrangement to said further container and in downstream connection with a said container comprising said sterol lipid; and comprising a second substrate not carrying an immobilised mycolic acid derived antigen, and a device for storage or transport of the treated samples.

11. A system for pre-treating a sample stream derived from a human or animal suspected of having active tuberculosis for use in the method of claim 1, which comprises a splitter for dividing said sample stream into at least a first and a second sample stream; at least a first and a second column, configured to receive said first and said second sample stream respectively; said first column comprising a compartment comprising a sterol lipid immobilized on a substrate, wherein said sterol lipid is cholesterol or a derivative thereof, and a further compartment comprising a first substrate carrying an immobilised mycolic acid derived antigen downstream of said compartment comprising said sterol lipid; and said second column comprising a compartment comprising said sterol lipid and a still further compartment comprising a second substrate not carrying an immobilised mycolic acid derived antigen downstream of said compartment comprising said sterol lipid; and a device for storage or transport of the treated samples passed through said columns.

12. A system for carrying out a method of detecting a marker for active tuberculosis in a sample derived from a human or animal suspected of having active tuberculosis according to the method of claim 1, which comprises a splitter for dividing said sample stream into at least a first and a second sample stream; at least a first and a second column, configured to receive said first and said second sample stream respectively; said first column comprising a compartment comprising a sterol lipid immobilised on a substrate, wherein said sterol lipid is cholesterol or a derivative thereof, and a further compartment comprising a first substrate carrying an immobilised mycolic acid derived antigen downstream of said compartment comprising said sterol lipid; and said second column comprising a compartment comprising said sterol lipid and a still further compartment comprising a second substrate not carrying an immobilised mycolic acid derived antigen downstream of said compartment comprising said sterol lipid and a first detection substrate carrying an immobilised mycolic acid derived antigen to receive at least part of the first sample stream and a second detection substrate carrying an immobilised mycolic acid derived antigen to receive at least part of the second sample stream.

13. The system according to claim 11, wherein said sterol lipid is immobilized on beads, and said first and second substrates are beads.

14. The system according to claim 12, wherein said sterol lipid is immobilized on beads, and said first and second substrates are beads.

15. The system according to claim 5, wherein the first and second detection substrates are a microporous membrane, preferably a nitrocellulose membrane.

16. The system according to claim 12, wherein the first and second detection substrates are a microporous membrane, preferably a nitrocellulose membrane.

17. The system according to claim 13, wherein the first and second detection substrates are a microporous membrane, preferably a nitrocellulose membrane.

18. The system according to claim 5, wherein the first and second detection substrate are formed by separate spots on the same membrane.

19. The system according to claim 12, wherein the first and second detection substrate are formed by separate spots on the same membrane.

20. The system according to claim 5, wherein said sterol lipid is immobilized on a substrate comprising said sterol lipid and a compound binding to cholesterol in the sample, such as pectin, amphothericin B or β-cyclodextrin.

21. The system according to claim 10, wherein said sterol lipid is immobilized on a substrate comprising said sterol lipid and a compound binding to cholesterol in the sample, such as pectin, amphothericin B or β-cyclodextrin.

22. The system according to claim 11, wherein said sterol lipid is immobilized on a substrate comprising said sterol lipid and a compound binding to cholesterol in the sample, such as pectin, amphothericin B or β-cyclodextrin.

23. The system according to claim 12, wherein said sterol lipid is immobilized on a substrate comprising said sterol lipid and a compound binding to cholesterol in the sample, such as pectin, amphothericin B or β-cyclodextrin.

24. A kit for use in diagnosing tuberculosis according to the method of claim 1, comprising:
one or more skin penetrators;
one or more tubings;
one or more containers coated with a sterol lipid immobilized on a substrate, wherein said sterol lipid is cholesterol or a derivative thereof, and optionally phosphatidyl choline, pectin, amphothericin B or β-cyclodextrin;
one or more containers comprising a substrate with and without an immobilised mycolic acid derived antigen;
one or more containers for transport and storage of samples and/or at least one microporous membrane with mycolic acid derived antigen immobilised thereon, and optionally secondary antibodies binding to the heavy chain of antibodies against mycolic acid derived antigens contained in a sample derived from a human or animal suspected of having active tuberculosis; or one or more biosensors comprising at least two chambers comprising a substrate with an immobilised mycolic acid derived antigen; and
optionally a diluent for diluting blood or plasma and/or a filter unit.

25. A kit for use in diagnosing tuberculosis according to the method of claim 1, comprising:
one or more skin penetrators;
one or more tubings;
one or more columns, comprising a compartment comprising a substrate coated with a sterol lipid and optionally phosphatidyl choline, pectin, amphothericin B or β-cyclodextrin; and
a compartment comprising a substrate coated with an immobilised mycolic acid derived antigen below said compartment comprising a substrate coated with a sterol lipid;
one or more columns, comprising a compartment comprising a substrate coated with a sterol lipid immobilized on a substrate, when said sterol lipid is cholesterol or a derivative thereof, and optionally phosphatidyl choline, pectin, amphothericin B or β-cyclodextrin; and
a compartment comprising a substrate coated without an immobilised mycolic acid derived antigen below said compartment comprising a substrate coated with a sterol lipid;
optionally one or more containers for transport and storage of samples;
optionally a diluent for diluting blood or plasma and/or a filter unit;
optionally at least one microporous membrane with mycolic acid derived antigen immobilised thereon;
and optionally secondary antibodies binding to the heavy chain of antibodies against mycolic acid derived antigens contained in a sample derived from a human or animal suspected of having active tuberculosis.

* * * * *